US007022328B1

(12) United States Patent
Panaccio et al.

(10) Patent No.: US 7,022,328 B1
(45) Date of Patent: Apr. 4, 2006

(54) THERAPEUTIC AND DIAGNOSTIC COMPOSITIONS

(75) Inventors: Michael Panaccio, North Balwyn (AU); Detlef Hasse, Sunbury (AU)

(73) Assignee: Australian Pork Limited, Australian Capital Territory (AU)

(*) Notice: Subject to any disclaimer, the term of this patent is extended or adjusted under 35 U.S.C. 154(b) by 0 days.

(21) Appl. No.: 09/077,574

(22) PCT Filed: Nov. 29, 1996

(86) PCT No.: PCT/AU96/00767

§ 371 (c)(1),
(2), (4) Date: Sep. 24, 1998

(87) PCT Pub. No.: WO97/20050

PCT Pub. Date: Jun. 5, 1997

(30) Foreign Application Priority Data

Nov. 30, 1995 (AU) .................................... PN6910
Nov. 30, 1995 (AU) .................................... PN6911

(51) Int. Cl.
*A61K 39/02* (2006.01)
*A61K 39/38* (2006.01)
*A61K 38/00* (2006.01)
*C07K 1/00* (2006.01)
*C07K 2/00* (2006.01)

(52) U.S. Cl. ............................. 424/234.1; 424/190.1; 424/184.1; 424/825; 530/350; 530/300; 530/825; 514/2

(58) Field of Classification Search ............... 530/350, 530/825, 300; 514/2; 424/184.1, 190.1, 424/234.1, 93.4, 825, 193.1
See application file for complete search history.

(56) References Cited

U.S. PATENT DOCUMENTS

| 5,610,059 A | 3/1997 | Joens et al. | ............... 435/252.1 |
| 5,714,375 A * | 2/1998 | Knittel et al. | ............ 435/252.1 |
| 6,379,677 B1 * | 4/2002 | Klesius et al. | ............ 424/244.1 |

FOREIGN PATENT DOCUMENTS

| WO | WO 94/26901 | 11/1994 |
| WO | WO 96/39629 | 12/1996 |

OTHER PUBLICATIONS

Lazar et al. Mol. Cellular Biol. 8: 1247-1252, 1988.*
Bowie et al. Science 247: 1306-1309, 1990.*
Burgess et al. J. Cell. Biol. 111: 2129-2138, 1990.*
Ellis RW. In: Vaccines. (Eds) Plotkin et al. W.B. Saunders Company, London, Chapter 29, 1988.*
McOrist et al. Infect. immun. 57: 957-962, 1989.*
McOrist et al. Inter. J. Systemic bacteriol. 45 (4): 820-825, Oct. 1995.*
Houghten et al. New Approaches to Immunization. Vaccines86, Cold Spring Harbor Laboratory, p. 21-25, 1986.*
Lemarchand et al. Vet. Pathol. 34: 152-156, Mar. 1997, abstract.*
C. Dale, et al., Identification and Sequencing of the groE Operon and Flanking Genes of *Lawsonia* . . . , Microbiology, vol. 144, pp. 2073-2084 (1998).
S. Suerbaum, et al., *Helicobacter phylori* hspA-hspB Heat-Shock Gene Cluster . . . , Molecular Microbiology, vol. 14(5), pp. 959-974 (1994).
B. Kansau, et al., Heat Shock Proteins of *Helicobacter pylori*, Aliment Pharmacol Ther., vol. 10:1, pp. 51-56 (1996).
Y. Wu, et al., Heat-Shock and Alkaline pH-Induced Proteins of *Campylobacter Jejuni* . . . , Infection and Immunity, vol. 61:10, pp. 4256-4260 (1994).
B. Dunn, et al., Identification and Purification of a cpn60 Heat Shock Protein . . . , Infection and Immunity, vol. 60:5, pp. 1946-1951 (1992).
D. Evans, et al., Urease-Associated Heat Shock Protein of *Helicobacter pylori*, Infection and Immunity, vol. 60:5, pp. 2125-2127 (1992).
T. Takata, et al., The Purification of a GroEL-Like Stress Protein from Aerobically Adapted·*Campylobacter jejuni*, Microbiol. Immunol., vol. 39:9, pp. 639-645 (1995).
N. Bukanov, et al., Ordered Cosmid Library and High-Resolution Physical-Genetic Map of *Helicobacter pylori* . . . , Molecular Microbiology, vol. 11:3, pp. 509-523 (1994).
Baqar S., et al., "Safety and immunogenicity of a prototype oral whole-cell killed *Campylobacter* vaccine administered with a mucosal adjuvant in non-human primates " Vaccine vol. 13, No. 1, pp. 22-28, 1995.
Guerry, P., et al., "Development and Characterization of recA Mutants of *Campylobacter jejuni* for Inclusion in Attenuated Vaccines" *Infection and Immunity* Feb. 1994, vol. 62, No. 2, pp. 426-463.

* cited by examiner

*Primary Examiner*—S. Devi
(74) *Attorney, Agent, or Firm*—Knobbe, Martens, Olson & Bear LLP

(57) ABSTRACT

The present invention relates generally to therapeutic compositions for the treatment and/or prophylaxis of intestinal disease conditions in animals and birds caused or exacerbated by *Lawsonia intracellularis* or similar or otherwise related microorganism. The present invention also contemplates methods for the treatment and/or prophylaxis of such intestinal disease conditions and to diagnostic agents and procedures for detecting *Lawsonia intracellularis* or similar or otherwise related microorganism.

10 Claims, 4 Drawing Sheets

SEQUENCE LISTING

<160> NUMBER OF SEQ ID NOS: 34

<210> SEQ ID NO 1
<211> LENGTH: 1647
<212> TYPE: DNA
<213> ORGANISM: Lawsonia intracellularis
<220> FEATURE:
<221> NAME/KEY: CDS
<222> LOCATION: (1)...(1644)

<400> SEQUENCE: 1

| | | | | | | | | | | | | | | | | |
|---|---|---|---|---|---|---|---|---|---|---|---|---|---|---|---|---|
| atg | gct | tct | aaa | gaa | atc | ctt | ttt | gat | gct | aaa | gcc | cgt | gaa | aaa | ctt | 48 |
| Met | Ala | Ser | Lys | Glu | Ile | Leu | Phe | Asp | Ala | Lys | Ala | Arg | Glu | Lys | Leu | |
| 1 | | | | 5 | | | | | 10 | | | | | 15 | | |
| tca | cga | ggt | gta | gat | aaa | ctt | gca | aat | gct | gtt | aaa | gta | aca | ctt | gga | 96 |
| Ser | Arg | Gly | Val | Asp | Lys | Leu | Ala | Asn | Ala | Val | Lys | Val | Thr | Leu | Gly | |
| | | | 20 | | | | | 25 | | | | | 30 | | | |
| cct | aaa | ggc | cgt | aat | gtc | gtt | att | gaa | aag | tct | ttt | ggt | tcc | cca | gtt | 144 |
| Pro | Lys | Gly | Arg | Asn | Val | Val | Ile | Glu | Lys | Ser | Phe | Gly | Ser | Pro | Val | |
| | | 35 | | | | | 40 | | | | | 45 | | | | |
| att | aca | aaa | gat | ggt | gta | tct | gtt | gca | aaa | gaa | att | gaa | ctt | gaa | gat | 192 |
| Ile | Thr | Lys | Asp | Gly | Val | Ser | Val | Ala | Lys | Glu | Ile | Glu | Leu | Glu | Asp | |
| | 50 | | | | | 55 | | | | | 60 | | | | | |
| aag | ttt | gaa | aat | atg | ggc | gct | caa | atg | gtt | aaa | gaa | gta | gct | ccc | aaa | 240 |
| Lys | Phe | Glu | Asn | Met | Gly | Ala | Gln | Met | Val | Lys | Glu | Val | Ala | Pro | Lys | |
| 65 | | | | | 70 | | | | | 75 | | | | | 80 | |
| act | agc | gat | att | gct | ggt | gat | gga | act | aca | aca | gca | aca | gtc | ctt | gca | 288 |
| Thr | Ser | Asp | Ile | Ala | Gly | Asp | Gly | Thr | Thr | Thr | Ala | Thr | Val | Leu | Ala | |
| | | | | 85 | | | | | 90 | | | | | 95 | | |
| caa | gct | att | tat | cgt | gaa | ggt | gta | aaa | ctt | gta | gca | gct | ggt | cgt | aat | 336 |
| Gln | Ala | Ile | Tyr | Arg | Glu | Gly | Val | Lys | Leu | Val | Ala | Ala | Gly | Arg | Asn | |
| | | | 100 | | | | | 105 | | | | | 110 | | | |
| cct | atg | gcc | att | aaa | cgt | ggc | ata | gat | aaa | gct | gtt | gtt | gct | gtt | act | 384 |
| Pro | Met | Ala | Ile | Lys | Arg | Gly | Ile | Asp | Lys | Ala | Val | Val | Ala | Val | Thr | |
| | | 115 | | | | | 120 | | | | | 125 | | | | |
| aaa | gaa | cta | agc | gac | att | aca | aag | cct | act | cgt | gac | caa | aaa | gaa | ata | 432 |
| Lys | Glu | Leu | Ser | Asp | Ile | Thr | Lys | Pro | Thr | Arg | Asp | Gln | Lys | Glu | Ile | |
| | 130 | | | | | 135 | | | | | 140 | | | | | |
| gct | caa | gtt | gga | acc | att | tct | gca | aac | tct | gat | aca | aca | ata | ggt | aat | 480 |
| Ala | Gln | Val | Gly | Thr | Ile | Ser | Ala | Asn | Ser | Asp | Thr | Thr | Ile | Gly | Asn | |
| 145 | | | | | 150 | | | | | 155 | | | | | 160 | |
| atc | ata | gct | gaa | gct | atg | gct | aaa | gtt | gga | aaa | gga | ggt | gtt | atc | aca | 528 |
| Ile | Ile | Ala | Glu | Ala | Met | Ala | Lys | Val | Gly | Lys | Gly | Gly | Val | Ile | Thr | |
| | | | | 165 | | | | | 170 | | | | | 175 | | |
| gtt | gag | gaa | gct | aaa | ggt | ctt | gaa | act | aca | tta | gat | gtg | gtt | gaa | gga | 576 |
| Val | Glu | Glu | Ala | Lys | Gly | Leu | Glu | Thr | Thr | Leu | Asp | Val | Val | Glu | Gly | |
| | | | 180 | | | | | 185 | | | | | 190 | | | |
| atg | aag | ttt | gac | cgt | ggc | tac | ctc | tct | cca | tac | ttt | gta | act | aat | cct | 624 |
| Met | Lys | Phe | Asp | Arg | Gly | Tyr | Leu | Ser | Pro | Tyr | Phe | Val | Thr | Asn | Pro | |
| | | 195 | | | | | 200 | | | | | 205 | | | | |
| gag | aaa | atg | gtt | tgt | gaa | ctt | gat | aac | cct | tat | atc | ctt | tgt | aat | gag | 672 |
| Glu | Lys | Met | Val | Cys | Glu | Leu | Asp | Asn | Pro | Tyr | Ile | Leu | Cys | Asn | Glu | |
| | 210 | | | | | 215 | | | | | 220 | | | | | |
| aaa | aag | att | act | agc | atg | aaa | gac | atg | cta | cca | atc | tta | gaa | caa | gtt | 720 |
| Lys | Lys | Ile | Thr | Ser | Met | Lys | Asp | Met | Leu | Pro | Ile | Leu | Glu | Gln | Val | |
| 225 | | | | | 230 | | | | | 235 | | | | | 240 | |
| gct | aaa | gta | aac | cgt | cca | ctc | ctt | att | att | gct | gaa | gac | gta | gaa | ggt | 768 |
| Ala | Lys | Val | Asn | Arg | Pro | Leu | Leu | Ile | Ile | Ala | Glu | Asp | Val | Glu | Gly | |
| | | | | 245 | | | | | 250 | | | | | 255 | | |

```
gaa gca ctt gca aca ctt gta gtc aat aag ctc cgt gga gca ctc caa       816
Glu Ala Leu Ala Thr Leu Val Val Asn Lys Leu Arg Gly Ala Leu Gln
        260                 265                 270 gtt gta gcc gta aaa gct cct ggt ttt ggt gaa cgc gta aaa gct atg       864
Val Val Ala Val Lys Ala Pro Gly Phe Gly Glu Arg Lys Ala Met
    275                 280                 285 ctt gaa gat att gct atc ctt act gga gaa gca ata ttt gaa gat           912
Leu Glu Asp Ile Ala Ile Leu Thr Gly Gly Glu Ala Ile Phe Glu Asp
        290                 295                 300 cgt ggt ata aag ctt gaa aat gta agc ttg tct tct tta gga aca gct       960
Arg Gly Ile Lys Leu Glu Asn Val Ser Leu Ser Ser Leu Gly Thr Ala
305                 310                 315                 320 aaa cgt gta gtt att gac aaa gaa aat act act atc gtt gat ggt gct      1008
Lys Arg Val Val Ile Asp Lys Glu Asn Thr Thr Ile Val Asp Gly Ala
                325                 330                 335 gga aaa tca gaa gat att aaa gct cga gtt aaa caa att cgt gca caa      1056
Gly Lys Ser Glu Asp Ile Lys Ala Arg Val Lys Gln Ile Arg Ala Gln
            340                 345                 350 att gaa gaa aca agc tca gat tat gat cgt gaa aaa ctt caa gaa cgt      1104
Ile Glu Glu Thr Ser Ser Asp Tyr Asp Arg Glu Lys Leu Gln Glu Arg
        355                 360                 365 ctt gca aaa ctt gtt ggt gga gta gct gtt atc cat gtt gga gct gct      1152
Leu Ala Lys Leu Val Gly Gly Val Ala Val Ile His Val Gly Ala Ala
    370                 375                 380 act gaa act gaa atg aaa gag aag aag gat cgt gta gaa gat gct cta      1200
Thr Glu Thr Glu Met Lys Glu Lys Lys Asp Arg Val Glu Asp Ala Leu
385                 390                 395                 400 aat gca aca aga gct gcg gtt gaa gaa ggt att gtc cct ggt ggt ggt      1248
Asn Ala Thr Arg Ala Ala Val Glu Glu Gly Ile Val Pro Gly Gly Gly
                405                 410                 415 act gct ttt gtc cgc tcc att aaa gtc ctt gat gat att aaa cct gct      1296
Thr Ala Phe Val Arg Ser Ile Lys Val Leu Asp Asp Ile Lys Pro Ala
            420                 425                 430 gat gat gat gaa ctt gct gga ctt aat atc atc cgt cgt tct ctt gaa      1344
Asp Asp Asp Glu Leu Ala Gly Leu Asn Ile Ile Arg Arg Ser Leu Glu
        435                 440                 445 gag cct tta cgt caa att gct gca aat gct ggc tat gaa ggt tct att      1392
Glu Pro Leu Arg Gln Ile Ala Ala Asn Ala Gly Tyr Glu Gly Ser Ile
    450                 455                 460 gtt gta gaa aaa gtt cgt gaa cca aaa gat ggt ttt gga ttt aat gct      1440
Val Val Glu Lys Val Arg Glu Pro Lys Asp Gly Phe Gly Phe Asn Ala
465                 470                 475                 480 gca tca gga gaa tat gaa gac ctt att aaa gct ggt gtc att gat cct      1488
Ala Ser Gly Glu Tyr Glu Asp Leu Ile Lys Ala Gly Val Ile Asp Pro
                485                 490                 495 aaa aaa gtt aca cgt att gca tta caa aat gca gca tca gta gcc tcc      1536
Lys Lys Val Thr Arg Ile Ala Leu Gln Asn Ala Ala Ser Val Ala Ser
            500                 505                 510 tta ctt cta act aca gaa tgc gct att gct gaa aaa cca gaa cct aaa      1584
Leu Leu Leu Thr Thr Glu Cys Ala Ile Ala Glu Lys Pro Glu Pro Lys
        515                 520                 525 aaa gat atg cct atg cct ggc ggt ggt atg ggt ggt atg ggt ggt atg      1632
Lys Asp Met Pro Met Pro Gly Gly Gly Met Gly Gly Met Gly Gly Met
    530                 535                 540 gac ggt atg tac tag                                                  1647
Asp Gly Met Tyr
545
```

```
<210> SEQ ID NO 2
<211> LENGTH: 548
<212> TYPE: PRT
<213> ORGANISM: Lawsonia intracellularis

<400> SEQUENCE: 2
```

| | | | | | | | | | | | | | | | |
|---|---|---|---|---|---|---|---|---|---|---|---|---|---|---|---|
| Met | Ala | Ser | Lys | Glu | Ile | Leu | Phe | Asp | Ala | Lys | Ala | Arg | Glu | Lys | Leu |
| 1 | | | | 5 | | | | | 10 | | | | | 15 | |
| Ser | Arg | Gly | Val | Asp | Lys | Leu | Ala | Asn | Ala | Val | Lys | Val | Thr | Leu | Gly |
| | | | 20 | | | | | 25 | | | | | 30 | | |
| Pro | Lys | Gly | Arg | Asn | Val | Val | Ile | Glu | Lys | Ser | Phe | Gly | Ser | Pro | Val |
| | | | 35 | | | | | 40 | | | | | 45 | | |
| Ile | Thr | Lys | Asp | Gly | Val | Ser | Val | Ala | Lys | Glu | Ile | Glu | Leu | Glu | Asp |
| | 50 | | | | | 55 | | | | | 60 | | | | |
| Lys | Phe | Glu | Asn | Met | Gly | Ala | Gln | Met | Val | Lys | Glu | Val | Ala | Pro | Lys |
| 65 | | | | | 70 | | | | | 75 | | | | | 80 |
| Thr | Ser | Asp | Ile | Ala | Gly | Asp | Gly | Thr | Thr | Thr | Ala | Thr | Val | Leu | Ala |
| | | | | 85 | | | | | 90 | | | | | 95 | |
| Gln | Ala | Ile | Tyr | Arg | Glu | Gly | Val | Lys | Leu | Val | Ala | Ala | Gly | Arg | Asn |
| | | | | 100 | | | | | 105 | | | | | 110 | |
| Pro | Met | Ala | Ile | Lys | Arg | Gly | Ile | Asp | Lys | Ala | Val | Val | Ala | Val | Thr |
| | | | 115 | | | | | 120 | | | | | 125 | | |
| Lys | Glu | Leu | Ser | Asp | Ile | Thr | Lys | Pro | Thr | Arg | Asp | Gln | Lys | Glu | Ile |
| | 130 | | | | | 135 | | | | | 140 | | | | |
| Ala | Gln | Val | Gly | Thr | Ile | Ser | Ala | Asn | Ser | Asp | Thr | Thr | Ile | Gly | Asn |
| 145 | | | | | 150 | | | | | 155 | | | | | 160 |
| Ile | Ile | Ala | Glu | Ala | Met | Ala | Lys | Val | Gly | Lys | Gly | Val | Ile | Thr |  |
| | | | | 165 | | | | | 170 | | | | | 175 | |
| Val | Glu | Glu | Ala | Lys | Gly | Leu | Glu | Thr | Thr | Leu | Asp | Val | Val | Glu | Gly |
| | | | | 180 | | | | | 185 | | | | | 190 | |
| Met | Lys | Phe | Asp | Arg | Gly | Tyr | Leu | Ser | Pro | Tyr | Phe | Val | Thr | Asn | Pro |
| | | | 195 | | | | | 200 | | | | | 205 | | |
| Glu | Lys | Met | Val | Cys | Glu | Leu | Asp | Asn | Pro | Tyr | Ile | Leu | Cys | Asn | Glu |
| | 210 | | | | | 215 | | | | | 220 | | | | |
| Lys | Lys | Ile | Thr | Ser | Met | Lys | Asp | Met | Leu | Pro | Ile | Leu | Glu | Gln | Val |
| 225 | | | | | 230 | | | | | 235 | | | | | 240 |
| Ala | Lys | Val | Asn | Arg | Pro | Leu | Leu | Ile | Ile | Ala | Glu | Asp | Val | Glu | Gly |
| | | | | 245 | | | | | 250 | | | | | 255 | |
| Glu | Ala | Leu | Ala | Thr | Leu | Val | Val | Asn | Lys | Leu | Arg | Gly | Ala | Leu | Gln |
| | | | | 260 | | | | | 265 | | | | | 270 | |
| Val | Val | Ala | Val | Lys | Ala | Pro | Gly | Phe | Gly | Glu | Arg | Arg | Lys | Ala | Met |
| | | | 275 | | | | | 280 | | | | | 285 | | |
| Leu | Glu | Asp | Ile | Ala | Ile | Leu | Thr | Gly | Gly | Glu | Ala | Ile | Phe | Glu | Asp |
| | 290 | | | | | 295 | | | | | 300 | | | | |
| Arg | Gly | Ile | Lys | Leu | Glu | Asn | Val | Ser | Leu | Ser | Ser | Leu | Gly | Thr | Ala |
| 305 | | | | | 310 | | | | | 315 | | | | | 320 |
| Lys | Arg | Val | Val | Ile | Asp | Lys | Glu | Asn | Thr | Thr | Ile | Val | Asp | Gly | Ala |
| | | | | 325 | | | | | 330 | | | | | 335 | |
| Gly | Lys | Ser | Glu | Asp | Ile | Lys | Ala | Arg | Val | Lys | Gln | Ile | Arg | Ala | Gln |
| | | | | 340 | | | | | 345 | | | | | 350 | |
| Ile | Glu | Glu | Thr | Ser | Ser | Asp | Tyr | Asp | Arg | Glu | Lys | Leu | Gln | Glu | Arg |
| | | | 355 | | | | | 360 | | | | | 365 | | |
| Leu | Ala | Lys | Leu | Val | Gly | Gly | Val | Ala | Val | Ile | His | Val | Gly | Ala | Ala |
| | 370 | | | | | 375 | | | | | 380 | | | | |

```
Thr Glu Thr Glu Met Lys Glu Lys Asp Arg Val Glu Asp Ala Leu
385                 390                 395                 400

Asn Ala Thr Arg Ala Ala Val Glu Glu Gly Ile Val Pro Gly Gly Gly
            405                 410                 415

Thr Ala Phe Val Arg Ser Ile Lys Val Leu Asp Asp Ile Lys Pro Ala
            420                 425                 430

Asp Asp Asp Glu Leu Ala Gly Leu Asn Ile Ile Arg Arg Ser Leu Glu
            435                 440                 445

Glu Pro Leu Arg Gln Ile Ala Ala Asn Ala Gly Tyr Glu Gly Ser Ile
        450                 455                 460

Val Val Glu Lys Val Arg Glu Pro Lys Asp Gly Phe Gly Phe Asn Ala
465                 470                 475                 480

Ala Ser Gly Glu Tyr Glu Asp Leu Ile Lys Ala Gly Val Ile Asp Pro
            485                 490                 495

Lys Lys Val Thr Arg Ile Ala Leu Gln Asn Ala Ala Ser Val Ala Ser
            500                 505                 510

Leu Leu Leu Thr Thr Glu Cys Ala Ile Ala Glu Lys Pro Glu Pro Lys
        515                 520                 525

Lys Asp Met Pro Met Pro Gly Gly Met Gly Gly Met Gly Gly Met
    530                 535                 540

Asp Gly Met Tyr
545

<210> SEQ ID NO 3
<211> LENGTH: 306
<212> TYPE: DNA
<213> ORGANISM: Lawsonia intracellularis
<220> FEATURE:
<221> NAME/KEY: CDS
<222> LOCATION: (1)...(303)

<400> SEQUENCE: 3 atg aac ctg aaa cct ttg aat gac cgt gtt tta gta aaa cgt ctt gaa      48
Met Asn Leu Lys Pro Leu Asn Asp Arg Val Leu Val Lys Arg Leu Glu
1               5                   10                  15 tct gaa gaa aaa aca gct ggt gga ctc tat atc cct gat act gct aaa      96
Ser Glu Glu Lys Thr Ala Gly Gly Leu Tyr Ile Pro Asp Thr Ala Lys
            20                  25                  30 gaa aaa cca tct cgt ggt gaa gtt gtt gct gtt gga cct ggt aaa cat     144
Glu Lys Pro Ser Arg Gly Glu Val Val Ala Val Gly Pro Gly Lys His
        35                  40                  45 aca gat gat ggt aaa tta ata cct atg gct gta aaa gca gga gat aca     192
Thr Asp Asp Gly Lys Leu Ile Pro Met Ala Val Lys Ala Gly Asp Thr
    50                  55                  60 gtt ctt ttt aat aag tat gca gga aca gaa gta aag ctt gat ggt gta     240
Val Leu Phe Asn Lys Tyr Ala Gly Thr Glu Val Lys Leu Asp Gly Val
65                  70                  75                  80 gag cat cta gtt atg cgt gaa gat gac atc cta gct gtt att act gga     288
Glu His Leu Val Met Arg Glu Asp Asp Ile Leu Ala Val Ile Thr Gly
                85                  90                  95 gaa act ggc cgc aag tga                                             306
Glu Thr Gly Arg Lys
            100

<210> SEQ ID NO 4
<211> LENGTH: 101
<212> TYPE: PRT
<213> ORGANISM: Lawsonia intracellularis
```

```
<400> SEQUENCE: 4

Met Asn Leu Lys Pro Leu Asn Asp Arg Val Leu Val Lys Arg Leu Glu
 1               5                  10                  15

Ser Glu Glu Lys Thr Ala Gly Gly Leu Tyr Ile Pro Asp Thr Ala Lys
            20                  25                  30

Glu Lys Pro Ser Arg Gly Glu Val Val Ala Val Gly Pro Gly Lys His
        35                  40                  45

Thr Asp Asp Gly Lys Leu Ile Pro Met Ala Val Lys Ala Gly Asp Thr
    50                  55                  60

Val Leu Phe Asn Lys Tyr Ala Gly Thr Glu Val Lys Leu Asp Gly Val
65                  70                  75                  80

Glu His Leu Val Met Arg Glu Asp Asp Ile Leu Ala Val Ile Thr Gly
                85                  90                  95

Glu Thr Gly Arg Lys
            100

<210> SEQ ID NO 5
<211> LENGTH: 4972
<212> TYPE: DNA
<213> ORGANISM: Lawsonia intracellularis
<220> FEATURE:
<221> NAME/KEY: misc_feature
<222> LOCATION: (1)...(4972)
<223> OTHER INFORMATION: n = A,T,C or G

<400> SEQUENCE: 5
```

| | | | | | |
|---|---|---|---|---|---|
| aactcctggt | ctatcaagat | caactaaaaa | atattcttta | tctaatagtt | gctcaaaaat     60 |
| aattgtacct | acaggtaaat | gaagaatcaa | atcttcccct | tttttaccat | gacgctggct    120 |
| cccctttacca | ccttctccat | tttgagctct | atagtgacgt | tgcacacgaa | aatcataaag    180 |
| ggttaacaaa | cgtgaatcag | ctttaaaaat | tatattacct | ccatctcctc | catcccctcc    240 |
| attaggtcca | cctttaggta | taaacttttc | gcgtctaaat | gaaacacatc | catttccacc    300 |
| ttttcctgcg | ctcacgctaa | tagttacttc | atcaacaaaa | cgcatgatta | tcctttcaat    360 |
| aacaaatatc | tattcaatac | tgttactaac | ttgtttactg | tttttctag | aaaattacct    420 |
| ggctaattat | tatagttata | tctagattaa | tgaaaaagga | agaagtcatt | acactccttc    480 |
| cttattaata | gaatcctgga | ataattatta | tacggtgggt | tgtatatgca | ctctactata    540 |
| tcttttacat | ttacgaaaat | atgtttcata | agttactata | ccattaactt | tgcaaataa    600 |
| agtatagtct | cttcccattc | caacattttc | tccaggatga | atttttgtac | ctagttgacg    660 |
| aacaaggata | ttgcctgcca | agactttctg | gccgccgaaa | cgctttatac | cacgacgttg    720 |
| tcctggacta | tctctaccat | tgcgagaact | tccaccagct | ttcttatggg | ccattttaat    780 |
| atctccttaa | agctgaatac | ctgttacttt | tagagctgta | tagtcttgac | gatgaccttg    840 |
| gagtttacgt | gagtcatttc | ttctccactt | tttaaaaaca | agaatttttt | tatcacgacc    900 |
| atgctcaaga | actttagcta | taactttagc | attattaata | tatggtgttc | caatttgagg    960 |
| agatgaacca | ccaatcataa | aaattttatc | aaaaaaaatt | tctgttccaa | cttcagcgtc   1020 |
| tattttagaa | acaaaaattt | tagaaccctc | ttcaacacag | aattgttttc | caccagcttc   1080 |
| aataattgcg | tacataaata | atgtgcctcc | caaaaaagac | aagaaatact | aatttgatat   1140 |
| tttcaatatt | gtcaagtagg | aactttatct | ttagaatgtt | agatgtaaca | atttttttag   1200 |
| aaaaaaaata | ttttcaatac | aataggaaaa | gaggaaaaaa | aaaagatttt | ttagaaaaaa   1260 |
| tttttattc | tccaaaaaat | gcaaaaatat | aaaaaattct | aataggatag | aagttattac   1320 |

```
tgtattgatt ttcaagactt acttaaaaat tttataaaa aaatttgcat tccctcttc    1380
ccaattccca tagagaagat tatttatcct aacgattggt ggacgctaag tccctgctgt   1440
tttgattata tatcaaatgt tgaaacaaat tttgtttagt ttcttttgt actctaaaaa   1500
gaagacaaaa aattctttat aaactgtaca ctctaaacaa aatagttcac aataaacagc   1560
aatacattat aattaattgg aggatactat tgtcatgaac ctgaaacctt tgaatgaccg   1620
tgttttagta aaacgtcttg aatctgaaga aaaaacagct ggtggactct atatccctga   1680
tactgctaaa gaaaaaccat ctcgtggtga agttgttgct gttggacctg gtaaacatac   1740
agatgatggt aaattaatac ctatggctgt aaaagcagga gatacagttc ttttaataa    1800
gtatgcagga acagaagtaa agcttgatgg tgtagagcat ctagttatgc gtgaagatga   1860
catcctagct gttattactg gagaaactgg ccgcaagtga aaaggcgta aataaaaga    1920
tcggtgatct ttaataattt tattcagtta taatgaaaac actaattaca cgcactctct   1980
gagaattttc tcagaaaact atatttaaca attctaaaat cgatatgttt ttaggaggaa   2040
aaccctaatg gcttctaaag aaatcctttt tgatgctaaa gcccgtgaaa actttcacg    2100
aggtgtagat aaacttgcaa atgctgttaa agtaacactt ggacctaaag gccgtaatgt   2160
cgttattgaa aagtctttg gttccccagt tattacaaaa gatggtgtat ctgttgcaaa   2220
agaaattgaa cttgaagata gtttgaaaa tatgggcgct caaatggtta agaagtagc    2280
tcccaaaact agcgatattg ctggtgatgg aactacaaca gcaacagtcc ttgcacaagc   2340
tatttatcgt gaaggtgtaa aacttgtagc agctggtcgt aatcctatgg ccattaaacg   2400
tggcatagat aaagctgttg ttgctgttac taaagaacta agcgacatta caaagcctac   2460
tcgtgaccaa aaagaaatag ctcaagttgg aaccatttct gcaaactctg atacaacaat   2520
aggtaatatc atagctgaag ctatggctaa agttggaaaa ggaggtgtta tcacagttga   2580
ggaagctaaa ggtctgaaa ctacattaga tgtggttgaa ggaatgaagt ttgaccgtgg    2640
ctacctctct ccatactttg taactaatcc tgagaaaatg gtttgtgaac ttgataaccc   2700
ttatatcctt tgtaatgaga aaagattac tagcatgaaa gacatgctac caatcttaga   2760
acaagttgct aaagtaaacc gtccactcct tattattgct gaagacgtag aaggtgaagc   2820
acttgcaaca cttgtagtca ataagctccg tgggagcactc caagttgtag ccgtaaaagc   2880
tcctggtttt ggtgaacgcc gtaaagctat gcttgaagat attgctatcc ttactggagg   2940
agaagcaata tttgaagatc gtggtataaa gcttgaaaat gtaagcttgt cttcttagg    3000
aacagctaaa cgtgtagtta ttgacaaaga aaatactact atcgttgatg gtgctggaaa   3060
atcagaagat attaaagctc gagttaaaca aattcgtgca caaattgaag aaacaagctc   3120
agattatgat cgtgaaaaac ttcaagaacg tcttgcaaaa cttgttggtg gagtagctgt   3180
tatccatgtt ggagctgcta ctgaaactga aatgaaagag aagaaggatc gtgtagaaga   3240
tgctctaaat gcaacaagag ctgcggttga agaaggtatt gtccctggtg gtggtactgc   3300
ttttgtccgc tccattaaag tccttgatga tattaaacct gctgatgatg atgaacttgc   3360
tggacttaat atcatccgtc gttctcttga agagccttta cgtcaaattg ctgcaaatgc   3420
tggctatgaa ggttctattg ttgtagaaaa agttcgtgaa ccaaaagatg gttttggatt   3480
taatgctgca tcaggagaat atgaagacct tattaaagct ggtgtcattg atcctaaaaa   3540
agttacacgt attgcattac aaaatgcagc atcagtagcc tccttacttc taactacaga   3600
atgcgctatt gctgaaaaac cagaacctaa aaaagatatg cctatgcctg gcggtggtat   3660
gggtggtatg ggtggtatgg acggtatgta ctagtcctat cttcagtaca acttagatgt   3720
```

-continued

```
ataaaaaccc cagaagcaat gcttccgggg ttttatactt tcagcataaa aaattaatat      3780
ttaatataca gacacattat tttggtattt attatttatt atgatcaaat atatagactg      3840
gatacaaaaa acaacaatga tgtttaaaaa ggcagggata gattcaccaa aactctctgc      3900
agaacttata ttaagtcatg ttttaaatat tacacgatta caaataataa tgactccttt      3960
tgaacctatt ccaactaata gctactcaac gcttaatgat atcatgttaa gaagactcca      4020
tggagaacca attgcatatc tcacagggaa aaaagaattt ttttcacgag aatttaaagt      4080
cactcaagcc acacttatcc ctcgcccaga gacagagtta cttatagaat ttgtattaaa      4140
ccatattaac ccaacacaac aaatatactt tgcagactta ggtacaggta gtgggtgtat      4200
tgcaattaca ctagctgctg aaagaaaaaa ttggttaggt attgctactg atatctctag      4260
tgaagcatta aaaatagcta aacttaatag ttttaaaaaat aacactcata gtcaactaca      4320
gtttcttcaa tcagatttta cacaaccact ctgtctaccc tcttcattag acttatatat      4380
cagtaatcct ccatatataa gtgaaaatga actgacctct cttccgcatg aagtaatatc      4440
ttttgaacct aaaatagctc ttacaccaca taaatgtatt catcttgatg aaataaatac      4500
cgttttacac tgctataaaa aaattattac ccaagcagag atatccctta agcctggagg      4560
aataataatt ttagaacatg gagcaacaca agcagaagct atcttattgt tgttaaaaaa      4620
caacatatgg acaaatgtaa taagtcatac tgatcttaca aataaaaatc gttttattac      4680
agcatataag tataaaatat aacttaatta tgttgkagaa aaaacaaaaa ataaaaataa      4740
gatattaaat attttttta ataaaattaa gcaattacta atatcttttt ttggrtcgtt      4800
yattgsatwa gaaactttgg rggrtrrcta tgaacaaaca accatncaac ggccaantac      4860
atnncaggnt tggggtcata ggggccacgc tttatgtacg tacaaccccn actgaaattc      4920
tggnttgntt tgggggnaa ntgggtatcg caacnctntc ccccccccct gg              4972
```

<210> SEQ ID NO 6
<211> LENGTH: 569
<212> TYPE: DNA
<213> ORGANISM: Lawsonia intracellularis
<220> FEATURE:
<221> NAME/KEY: CDS
<222> LOCATION: (209)...(244)
<221> NAME/KEY: CDS
<222> LOCATION: (248)...(568)
<221> NAME/KEY: misc_feature
<222> LOCATION: (1)...(569)
<223> OTHER INFORMATION: n = A,T,C or G

<400> SEQUENCE: 6

```
ggttaaaaag taaggagaaa aggttggtta aaccaagttt aaaaaattaa ttttttttta       60
ttacccaaaa aagtttatta gattaagtaa tattaatttg gcccaaaaat ttttttgggc      120
atgggttttt tgcttttaaa atagagatgt gtaggtaaca ttttttcctc catgaaatta      180 tttttttagga gatgttatca tgatgggg agt ttg ttt att gnt gcg aac agg       232
                                Ser Leu Phe Ile Xaa Ala Asn Arg
                                  1               5 tat gaa aac cca tag nac agg gnt ggt act gtc tcc aat aat att gct        280
Tyr Glu Asn Pro     Xaa Arg Xaa Gly Thr Val Ser Asn Asn Ile Ala
     10               15                   20 aac gca aat acc att ggg tat aag cag caa cag gta gtg ttt caa gac        328
Asn Ala Asn Thr Ile Gly Tyr Lys Gln Gln Gln Val Val Phe Gln Asp
     25               30                   35 ctg ttt agt caa gat tta gca ata ggt ttt act gga agt cag ggg cca        376
Leu Phe Ser Gln Asp Leu Ala Ile Gly Phe Thr Gly Ser Gln Gly Pro
 40               45                   50                  55
```

-continued

```
aac cag gct ggt atg gga gca cag gtg gga agt gtt cgc aca att ttt     424
Asn Gln Ala Gly Met Gly Ala Gln Val Gly Ser Val Arg Thr Ile Phe
            60                  65                  70 aca cag ggt gct ttt gaa cct ggc aat agt gta aca gat cct gct att     472
Thr Gln Gly Ala Phe Glu Pro Gly Asn Ser Val Thr Asp Pro Ala Ile
        75                  80                  85 ggt gga aaa ggt ttt ttt cag gtt aca tta gag gat aaa gta cac tat     520
Gly Gly Lys Gly Phe Phe Gln Val Thr Leu Glu Asp Lys Val His Tyr
    90                  95                  100 aca cga gca ggg aat ttt cgt ttt act caa gat ggt ttt tta aat gat     568
Thr Arg Ala Gly Asn Phe Arg Phe Thr Gln Asp Gly Phe Leu Asn Asp
    105                 110                 115 c                                                                   569
```

<210> SEQ ID NO 7
<211> LENGTH: 12
<212> TYPE: PRT
<213> ORGANISM: Lawsonia intracellularis
<220> FEATURE:
<221> NAME/KEY: VARIANT
<222> LOCATION: (1)...(12)
<223> OTHER INFORMATION: Xaa = Any Amino Acid

<400> SEQUENCE: 7

Ser Leu Phe Ile Xaa Ala Asn Arg Tyr Glu Asn Pro
1               5                   10

<210> SEQ ID NO 8
<211> LENGTH: 107
<212> TYPE: PRT
<213> ORGANISM: Lawsonia intracellularis
<220> FEATURE:
<221> NAME/KEY: VARIANT
<222> LOCATION: (1)...(107)
<223> OTHER INFORMATION: Xaa = Any Amino Acid

<400> SEQUENCE: 8

Xaa Arg Xaa Gly Thr Val Ser Asn Asn Ile Ala Asn Ala Asn Thr Ile
1               5                   10                  15

Gly Tyr Lys Gln Gln Gln Val Val Phe Gln Asp Leu Phe Ser Gln Asp
            20                  25                  30

Leu Ala Ile Gly Phe Thr Gly Ser Gln Gly Pro Asn Gln Ala Gly Met
        35                  40                  45

Gly Ala Gln Val Gly Ser Val Arg Thr Ile Phe Thr Gln Gly Ala Phe
    50                  55                  60

Glu Pro Gly Asn Ser Val Thr Asp Pro Ala Ile Gly Gly Lys Gly Phe
65                  70                  75                  80

Phe Gln Val Thr Leu Glu Asp Lys Val His Tyr Thr Arg Ala Gly Asn
                85                  90                  95

Phe Arg Phe Thr Gln Asp Gly Phe Leu Asn Asp
            100                 105

<210> SEQ ID NO 9
<211> LENGTH: 1450
<212> TYPE: DNA
<213> ORGANISM: Lawsonia intracellularis
<220> FEATURE:
<221> NAME/KEY: CDS
<222> LOCATION: (3)...(410)
<221> NAME/KEY: CDS
<222> LOCATION: (1080)...(1448)
<221> NAME/KEY: misc_feature
<222> LOCATION: (1)...(1450)
<223> OTHER INFORMATION: n = A,T,C or G

<400> SEQUENCE: 9

```
ga tct aaa gag tct aca tat att gcc cga att gaa aat tct aca agt      47
   Ser Lys Glu Ser Thr Tyr Ile Ala Arg Ile Glu Asn Ser Thr Ser
    1               5                  10                  15 gaa aaa aca cta aat gat ctt gat ata ctt tta aaa gat gtg atg tta      95
Glu Lys Thr Leu Asn Asp Leu Asp Ile Leu Leu Lys Asp Val Met Leu
                20                  25                  30 aca tca aaa aag cat gaa tca cgt aga ctt gca gag tct gta cat caa     143
Thr Ser Lys Lys His Glu Ser Arg Arg Leu Ala Glu Ser Val His Gln
        35                  40                  45 aat att ctt acc cac ctt ata caa aaa aat tat aat act cac aat ggt     191
Asn Ile Leu Thr His Leu Ile Gln Lys Asn Tyr Asn Thr His Asn Gly
    50                  55                  60 ggg ata aaa tct gca cct ttt cat gtt ctt ata gga ccc aaa ata cca     239
Gly Ile Lys Ser Ala Pro Phe His Val Leu Ile Gly Pro Lys Ile Pro
65                  70                  75 agt att ctt gtt gaa gta ggt tac tgt agt aat aaa gct gaa gca cag     287
Ser Ile Leu Val Glu Val Gly Tyr Cys Ser Asn Lys Ala Glu Ala Gln
 80                  85                  90                  95 cgt ctg gca tct agt aat tac caa aaa gca tta ata gaa gga tta gct     335
Arg Leu Ala Ser Ser Asn Tyr Gln Lys Ala Leu Ile Glu Gly Leu Ala
                100                 105                 110 aaa ggt att ttc tgt tac cta aaa aaa cta cat cac ctt gat att tac     383
Lys Gly Ile Phe Cys Tyr Leu Lys Lys Leu His His Leu Asp Ile Tyr
        115                 120                 125 tct agt ttt aty cta tct aat tgc act taatagcttg gacaattatt           430
Ser Ser Phe Xaa Leu Ser Asn Cys Thr
        130                 135 atatgaaggg tatccatgtg aaggtacctg gttaagcttt taaatgtaaa aattatgcaa   490
ccatacytta ttccttcaga ggagcttcat tatgaaagta aaaactcttt ccatggctat   550
tttagcttgt ttattagtag ctaacagtgc attttcggct gacttcccta ttggtgtctt   610
taattctcaa tccattgcca tggagagtga agcagctaag gccgctcaaa aaaaattaca   670
atcagaattt ggtaatgaaa aaacacaact tgaaaacaag caaaagwttg cmaacaaaag   730
ctgatgattt acaagctwag tcagcagcta tgtytaacca agcacgtgaa gataaacaaa   790
gagaatttct tgaacttcgt cgtaatttcg aagaaaaaty tcgtgacttt gcaatacgtg   850
tcgaacaagc tgaaaacaca ttacgtcaat atntagctga acaaatntat nttgctgctg   910
aaactatagc aaaaaagaaa gggttaaact tgttttgata gtgttaggga agtgtaatgt   970
accttgaaaa aaatttagat attacaaaga aattyttgaa gccataaatg ctgcatggaa  1030 aaaggtgga agtaaacttc cagagatggc aaaccggaaa aaataacag atg ccc cag  1088
                                                     Met Pro Gln tat aaa ctt tca gaa att gct aaa ctt tta aac tta aca tta caa ggt    1136
Tyr Lys Leu Ser Glu Ile Ala Lys Leu Leu Asn Leu Thr Leu Gln Gly
140                 145                 150                 155 gat gat att gaa gtt gta ggc gta aat aca ctt caa gat gca tca cca    1184
Asp Asp Ile Glu Val Val Gly Val Asn Thr Leu Gln Asp Ala Ser Pro
                160                 165                 170 aat gag ata agt ttt cta gca aat gct aaa tat att cac cag ctt gtt    1232
Asn Glu Ile Ser Phe Leu Ala Asn Ala Lys Tyr Ile His Gln Leu Val
        175                 180                 185 ttg tca cag gct ggt gct att att ctt tca aaa gaa tat gct agt cgt    1280
Leu Ser Gln Ala Gly Ala Ile Ile Leu Ser Lys Glu Tyr Ala Ser Arg
    190                 195                 200
```

-continued

```
gtt cca cga gca cta atc agt act gaa cca tat aga gat ttt ggt aga      1328
Val Pro Arg Ala Leu Ile Ser Thr Glu Pro Tyr Arg Asp Phe Gly Arg
    205                 210                 215
gtt ctt tct tta ttc tct ata cct caa gga tgt ttt gat ggt ata agt      1376
Val Leu Ser Leu Phe Ser Ile Pro Gln Gly Cys Phe Asp Gly Ile Ser
220                 225                 230                 235
cat caa gct tat ata cac cct aca gca caa gtc tct aaa aca gct act      1424
His Gln Ala Tyr Ile His Pro Thr Ala Gln Val Ser Lys Thr Ala Thr
                240                 245                 250
atc tat cct ttn gtt ttt ata gga tc                                   1450
Ile Tyr Pro Xaa Val Phe Ile Gly
            255

<210> SEQ ID NO 10
<211> LENGTH: 136
<212> TYPE: PRT
<213> ORGANISM: Lawsonia intracellularis
<220> FEATURE:
<221> NAME/KEY: VARIANT
<222> LOCATION: (1)...(136)
<223> OTHER INFORMATION: Xaa = Any Amino Acid

<400> SEQUENCE: 10

Ser Lys Glu Ser Thr Tyr Ile Ala Arg Ile Glu Asn Ser Thr Ser Glu
 1               5                  10                  15

Lys Thr Leu Asn Asp Leu Asp Ile Leu Leu Lys Asp Val Met Leu Thr
            20                  25                  30

Ser Lys Lys His Glu Ser Arg Arg Leu Ala Glu Ser Val His Gln Asn
        35                  40                  45

Ile Leu Thr His Leu Ile Gln Lys Asn Tyr Asn Thr His Asn Gly Gly
    50                  55                  60

Ile Lys Ser Ala Pro Phe His Val Leu Ile Gly Pro Lys Ile Pro Ser
65                  70                  75                  80

Ile Leu Val Glu Val Gly Tyr Cys Ser Asn Lys Ala Glu Ala Gln Arg
                85                  90                  95

Leu Ala Ser Ser Asn Tyr Gln Lys Ala Leu Ile Glu Gly Leu Ala Lys
            100                 105                 110

Gly Ile Phe Cys Tyr Leu Lys Lys Leu His His Leu Asp Ile Tyr Ser
        115                 120                 125

Ser Phe Xaa Leu Ser Asn Cys Thr
    130                 135

<210> SEQ ID NO 11
<211> LENGTH: 123
<212> TYPE: PRT
<213> ORGANISM: Lawsonia intracellularis
<220> FEATURE:
<221> NAME/KEY: VARIANT
<222> LOCATION: (1)...(123)
<223> OTHER INFORMATION: Xaa = Any Amino Acid

<400> SEQUENCE: 11

Met Pro Gln Tyr Lys Leu Ser Glu Ile Ala Lys Leu Leu Asn Leu Thr
 1               5                  10                  15

Leu Gln Gly Asp Asp Ile Glu Val Val Gly Val Asn Thr Leu Gln Asp
            20                  25                  30

Ala Ser Pro Asn Glu Ile Ser Phe Leu Ala Asn Ala Lys Tyr Ile His
        35                  40                  45

Gln Leu Val Leu Ser Gln Ala Gly Ala Ile Ile Leu Ser Lys Glu Tyr
    50                  55                  60
```

-continued

```
Ala Ser Arg Val Pro Arg Ala Leu Ile Ser Thr Glu Pro Tyr Arg Asp
 65              70                  75                  80

Phe Gly Arg Val Leu Ser Leu Phe Ser Ile Pro Gln Gly Cys Phe Asp
                 85                  90                  95

Gly Ile Ser His Gln Ala Tyr Ile His Pro Thr Ala Gln Val Ser Lys
            100                 105                 110

Thr Ala Thr Ile Tyr Pro Xaa Val Phe Ile Gly
        115                 120

<210> SEQ ID NO 12
<211> LENGTH: 559
<212> TYPE: DNA
<213> ORGANISM: Lawsonia intracellularis
<220> FEATURE:
<221> NAME/KEY: CDS
<222> LOCATION: (3)...(296)
<221> NAME/KEY: CDS
<222> LOCATION: (300)...(557)
<221> NAME/KEY: misc_feature
<222> LOCATION: (1)...(559)
<223> OTHER INFORMATION: n = A,T,C or G

<400> SEQUENCE: 12 ga tca aag ccg cat tta cng caa gag tta gaa att gaa gtt ttg aaa        47
   Ser Lys Pro His Leu Xaa Gln Glu Leu Glu Ile Glu Val Leu Lys
    1               5                  10                  15 aaa gaa gac ttt ggg cgt cat att gtt aaa tta tgc tgg aaa ggt tct       95
Lys Glu Asp Phe Gly Arg His Ile Val Lys Leu Cys Trp Lys Gly Ser
             20                  25                  30 tta tca aat atc ttt ttt tcc tat ggg gat atc ccg cac cca cct tat      143
Leu Ser Asn Ile Phe Phe Ser Tyr Gly Asp Ile Pro His Pro Pro Tyr
         35                  40                  45 ata cat caa agt aat aag gtt cag gat aag gaa aga tat cnt acn gta      191
Ile His Gln Ser Asn Lys Val Gln Asp Lys Glu Arg Tyr Xaa Thr Val
     50                  55                  60 tac tct ata tta cat aan ctg ggt tct gta gca gct cct aca gct gga      239
Tyr Ser Ile Leu His Xaa Leu Gly Ser Val Ala Ala Pro Thr Ala Gly
 65                  70                  75 tta cnc ttt tct gaa act agc cgt nat aaa tta cac aaa nat ggt att      287
Leu Xaa Phe Ser Glu Thr Ser Arg Xaa Lys Leu His Lys Xaa Gly Ile
 80                  85                  90                  95 agt tgg gca taa atc cct ctt cac gtg gga tat gga aca ttc agt ccc      335
Ser Trp Ala     Ile Pro Leu His Val Gly Tyr Gly Thr Phe Ser Pro
                    100                 105                 110 gtc ctc tgc aat gac atc cca aaa cat ctt atc cnt tct gag ttt gtt      383
Val Leu Cys Asn Asp Ile Pro Lys His Leu Ile Xaa Ser Glu Phe Val
            115                 120                 125 cac ttt cct gaa act acn ttt tcc act ata tta aat gca cgg ttt gca      431
His Phe Pro Glu Thr Thr Phe Ser Thr Ile Leu Asn Ala Arg Phe Ala
        130                 135                 140 ngg gaa tac cta tgt tct gcc ata ggg gac cca ctg ttg tcc cca cca      479
Xaa Glu Tyr Leu Cys Ser Ala Ile Gly Asp Pro Leu Leu Ser Pro Pro
    145                 150                 155 ttg gan ggg tgt tat ctt acc cct ttc gcc cgg ggt tcc cct ccc caa      527
Leu Xaa Gly Cys Tyr Leu Thr Pro Phe Ala Arg Gly Ser Pro Pro Gln
160                 165                 170 ccc tat tcc att gng ttt tcc tct caa att at                           559
Pro Tyr Ser Ile Xaa Phe Ser Ser Gln Ile
175                 180
```

```
<210> SEQ ID NO 13
<211> LENGTH: 98
<212> TYPE: PRT
<213> ORGANISM: Lawsonia intracellularis
<220> FEATURE:
<221> NAME/KEY: VARIANT
<222> LOCATION: (1)...(98)
<223> OTHER INFORMATION: Xaa = Any Amino Acid

<400> SEQUENCE: 13

Ser Lys Pro His Leu Xaa Gln Glu Leu Glu Ile Val Leu Lys Lys
 1               5                  10                  15

Glu Asp Phe Gly Arg His Ile Val Lys Leu Cys Trp Lys Gly Ser Leu
                20                  25                  30

Ser Asn Ile Phe Phe Ser Tyr Gly Asp Ile Pro His Pro Pro Tyr Ile
            35                  40                  45

His Gln Ser Asn Lys Val Gln Asp Lys Glu Arg Tyr Xaa Xaa Val Tyr
        50                  55                  60

Ser Ile Leu His Xaa Leu Gly Ser Val Ala Ala Pro Thr Ala Gly Leu
65                  70                  75                  80

Xaa Phe Ser Glu Thr Ser Arg Xaa Lys Leu His Lys Xaa Gly Ile Ser
                85                  90                  95

Trp Ala

<210> SEQ ID NO 14
<211> LENGTH: 86
<212> TYPE: PRT
<213> ORGANISM: Lawsonia intracellularis
<220> FEATURE:
<221> NAME/KEY: VARIANT
<222> LOCATION: (1)...(86)
<223> OTHER INFORMATION: Xaa = Any Amino Acid

<400> SEQUENCE: 14

Ile Pro Leu His Val Gly Tyr Gly Thr Phe Ser Pro Val Leu Cys Asn
 1               5                  10                  15

Asp Ile Pro Lys His Leu Ile Xaa Ser Glu Phe Val His Phe Pro Glu
                20                  25                  30

Thr Xaa Phe Ser Thr Ile Leu Asn Ala Arg Phe Ala Xaa Glu Tyr Leu
            35                  40                  45

Lys Ser Ala Ile Gly Asp Pro Leu Leu Ser Pro Pro Leu Xaa Gly Cys
        50                  55                  60

Tyr Leu Thr Pro Phe Ala Arg Gly Ser Pro Pro Gln Pro Tyr Ser Ile
65                  70                  75                  80

Xaa Phe Ser Ser Gln Ile
                85

<210> SEQ ID NO 15
<211> LENGTH: 477
<212> TYPE: DNA
<213> ORGANISM: Lawsonia intracellularis
<220> FEATURE:
<221> NAME/KEY: CDS
<222> LOCATION: (2)...(10)
<221> NAME/KEY: CDS
<222> LOCATION: (14)...(178)
<221> NAME/KEY: CDS
<222> LOCATION: (182)...(220)
<221> NAME/KEY: CDS
<222> LOCATION: (224)...(256)
<221> NAME/KEY: CDS
<222> LOCATION: (269)...(295)
```

```
<221> NAME/KEY: misc_feature
<222> LOCATION: (1)...(477)
<223> OTHER INFORMATION: n = A,T,C or G

<400> SEQUENCE: 15
```

| | | | | | | | | | | | | | | | | |
|---|---|---|---|---|---|---|---|---|---|---|---|---|---|---|---|---|
|t ata|aaa|cat|tag|cgn|ctt|tng|tat|ttg|gac|ttc|aaa|aaa|att|ttt|aat|49|
| Ile|Lys|His| |Arg|Leu|Xaa|Tyr|Leu|Asp|Phe|Lys|Lys|Ile|Phe|Asn| |
|  1| | | |  5| | | | | 10| | | | | 15| | |

| | | | | | | | | | | | | | | |
|---|---|---|---|---|---|---|---|---|---|---|---|---|---|---|
|tat|ata|gga|gaa|cat|tca|cca|tta|aaa|cgt|aat|gta|ant|atg|gaa gat|97|
|Tyr|Ile|Gly|Glu|His|Ser|Pro|Leu|Lys|Arg|Asn|Val|Xaa|Met|Glu Asp|
| | | | 20| | | | | 25| | | | | 30| | |

| | | | | | | | | | | | | | | |
|---|---|---|---|---|---|---|---|---|---|---|---|---|---|---|
|gta|ggt|aaa|tct|gct|gtt|ttt|tta|gct|tca|gac|ctn|tca|tca|gga gta|145|
|Val|Gly|Lys|Ser|Ala|Val|Phe|Leu|Ala|Ser|Asp|Leu|Ser|Ser|Gly Val|
| | | | 35| | | | | 40| | | | | 45| | |

```
acc gtt gaa ttn ttt ttg ttg atg ctg gna caa taa ttt agg tat tta    193
Thr Gly Glu Xaa Phe Leu Leu Met Leu Xaa Gln     Phe Arg Tyr Leu
         50                  55                      60 acc ata cat gct tta tac aac ata ttg tga gtt aca ata gcc ata aca    241
Thr Ile His Ala Leu Tyr Asn Ile Leu     Val Thr Ile Ala Ile Thr
         65                  70                      75 cat tta tat tct ata taataacagt ag aat aat aat aga ata ttt ttt atg  292
His Leu Tyr Ser Ile              Asn Asn Asn Arg Ile Phe Phe Met
         80                           85                      90 acc atttgtatct atacaatagt aaatagatta atacataaa gactatattc          345
Thr tttttgagag caacttaaag gagcggttat ggctttagtt acaaaagaag aagtacttca  405
ataccatagt gaaccccgac caggtaaact tgaagtattt tctataaaac catgtaaaac  465
acaaaaagat cc                                                     477

<210> SEQ ID NO 16
<211> LENGTH: 3
<212> TYPE: PRT
<213> ORGANISM: Lawsonia intracellularis

<400> SEQUENCE: 16

Ile Lys His
 1

<210> SEQ ID NO 17
<211> LENGTH: 55
<212> TYPE: PRT
<213> ORGANISM: Lawsonia intracellularis
<220> FEATURE:
<221> NAME/KEY: VARIANT
<222> LOCATION: (1)...(55)
<223> OTHER INFORMATION: Xaa = Any Amino Acid

<400> SEQUENCE: 17

Xaa Leu Xaa Tyr Leu Asp Phe Lys Lys Ile Phe Asn Tyr Ile Gly Glu
 1               5                  10                  15

His Ser Pro Leu Lys Arg Asn Val Xaa Met Glu Asp Val Gly Lys Ser
             20                  25                  30

Ala Val Phe Leu Ala Ser Asp Xaa Ser Ser Gly Val Thr Gly Glu Xaa
         35                  40                  45

Phe Leu Leu Met Leu Xaa Gln
     50                  55

<210> SEQ ID NO 18
<211> LENGTH: 13
<212> TYPE: PRT
<213> ORGANISM: Lawsonia intracellularis
```

-continued

```
<400> SEQUENCE: 18

Phe Arg Tyr Leu Thr Ile His Ala Leu Tyr Asn Ile Leu
1               5                   10

<210> SEQ ID NO 19
<211> LENGTH: 11
<212> TYPE: PRT
<213> ORGANISM: Lawsonia intracellularis

<400> SEQUENCE: 19

Val Thr Ile Ala Ile Thr His Leu Tyr Ser Ile
1               5                   10

<210> SEQ ID NO 20
<211> LENGTH: 9
<212> TYPE: PRT
<213> ORGANISM: Lawsonia intracellularis

<400> SEQUENCE: 20

Asn Asn Asn Arg Ile Phe Phe Met Thr
1               5

<210> SEQ ID NO 21
<211> LENGTH: 525
<212> TYPE: DNA
<213> ORGANISM: Lawsonia intracellularis
<220> FEATURE:
<221> NAME/KEY: CDS
<222> LOCATION: (2)...(352)
<221> NAME/KEY: CDS
<222> LOCATION: (356)...(361)
<221> NAME/KEY: CDS
<222> LOCATION: (365)...(409)
<221> NAME/KEY: CDS
<222> LOCATION: (413)...(433)
<221> NAME/KEY: CDS
<222> LOCATION: (437)...(451)
<221> NAME/KEY: CDS
<222> LOCATION: (455)...(523)

<400> SEQUENCE: 21 g gaa ttg tta gta ttc tcc cag aac aga agc caa aat att tgg cta ctt        49
  Glu Leu Leu Val Phe Ser Gln Asn Arg Ser Gln Asn Ile Trp Leu Leu
  1               5                   10                  15 aca tta cct att ttt gtg tta ggt ata gca caa ggt ata tca ttt cct        97
Thr Leu Pro Ile Phe Val Leu Gly Ile Ala Gln Gly Ile Ser Phe Pro
                20                  25                  30 tta gta aac agc cac att aca tca ctt gca cca aca tcc aac aga gct       145
Leu Val Asn Ser His Ile Thr Ser Leu Ala Pro Thr Ser Asn Arg Ala
            35                  40                  45 att gtt atg gct ata aac agt aca ttt atg agg tta agt cag agt att       193
Ile Val Met Ala Ile Asn Ser Thr Phe Met Arg Leu Ser Gln Ser Ile
        50                  55                  60 tcg caa atg gtt ttt ggt att gga tgg tca ttt ttt ggt tgg cct ggt       241
Ser Gln Met Val Phe Gly Ile Gly Trp Ser Phe Phe Gly Trp Pro Gly
    65                  70                  75                  80 cct ttt ata ttt ggt ctt ttt act tct att ata tta gcc ctc tta att       289
Pro Phe Ile Phe Gly Leu Phe Thr Ser Ile Ile Leu Ala Leu Leu Ile
                85                  90                  95 atg aag tat ttt caa gat gta acc caa tat cac cta ttt ttg ata agt       337
Met Lys Tyr Phe Gln Asp Val Thr Gln Tyr His Leu Phe Leu Ile Ser
            100                 105                 110 agt aaa ttt tat tat taa aaa gct tag tta gtt aag att aca tat att       385
Ser Lys Phe Tyr Tyr     Lys Ala     Leu Val Lys Ile Thr Tyr Ile
        115                 120                 125
```

```
ata tac aat tac tat aac att aac taa tta cta act att act tcc aat    433
Ile Tyr Asn Tyr Tyr Asn Ile Asn     Leu Leu Thr Ile Thr Ser Asn
            130                 135                 140 tga tta att gat gct att taa aga gga tat att aat gat gtc atg gct    481
    Leu Ile Asp Ala Ile     Arg Gly Tyr Ile Asn Asp Val Met Ala
                145                     150                 155 cac aat agg tgt tat cct tgg att agt gca tgg gat cca ggt            523
His Asn Arg Cys Tyr Pro Trp Ile Ser Ala Trp Asp Pro Gly
                160                 165 cc                                                                 525
```

<210> SEQ ID NO 22
<211> LENGTH: 117
<212> TYPE: PRT
<213> ORGANISM: Lawsonia intracellularis

<400> SEQUENCE: 22

```
Glu Leu Leu Val Phe Ser Gln Asn Arg Ser Gln Asn Ile Trp Leu Leu
1               5                   10                  15

Thr Leu Pro Ile Phe Val Leu Gly Ile Ala Gln Gly Ile Ser Phe Pro
            20                  25                  30

Leu Val Asn Ser His Ile Thr Ser Leu Ala Pro Thr Ser Asn Arg Ala
        35                  40                  45

Ile Val Met Ala Ile Asn Ser Thr Phe Met Arg Leu Ser Gln Ser Ile
    50                  55                  60

Ser Gln Met Val Phe Gly Ile Gly Trp Ser Phe Gly Trp Pro Gly
65                  70                  75                  80

Pro Phe Ile Phe Gly Leu Phe Thr Ser Ile Ile Leu Ala Leu Leu Ile
                85                  90                  95

Met Lys Tyr Phe Gln Asp Val Thr Gln Tyr His Leu Phe Leu Ile Ser
            100                 105                 110

Ser Lys Phe Tyr Tyr
        115
```

<210> SEQ ID NO 23
<211> LENGTH: 2
<212> TYPE: PRT
<213> ORGANISM: Lawsonia intracellularis

<400> SEQUENCE: 23

```
Lys Ala
1
```

<210> SEQ ID NO 24
<211> LENGTH: 15
<212> TYPE: PRT
<213> ORGANISM: Lawsonia intracellularis

<400> SEQUENCE: 24

```
Leu Val Lys Ile Thr Tyr Ile Ile Tyr Asn Tyr Asn Ile Asn
1               5                   10                  15
```

<210> SEQ ID NO 25
<211> LENGTH: 7
<212> TYPE: PRT
<213> ORGANISM: Lawsonia intracellularis

<400> SEQUENCE: 25

```
Leu Leu Thr Ile Thr Ser Asn
1               5
```

<210> SEQ ID NO 26
<211> LENGTH: 5
<212> TYPE: PRT
<213> ORGANISM: Lawsonia intracellularis

<400> SEQUENCE: 26

Leu Ile Asp Ala Ile
 1               5

<210> SEQ ID NO 27
<211> LENGTH: 23
<212> TYPE: PRT
<213> ORGANISM: Lawsonia intracellularis

<400> SEQUENCE: 27

Arg Gly Tyr Ile Asn Asp Val Met Ala His Asn Arg Cys Tyr Pro Trp
 1               5                  10                  15

Ile Ser Ala Trp Asp Pro Gly
            20

<210> SEQ ID NO 28
<211> LENGTH: 846
<212> TYPE: DNA
<213> ORGANISM: Lawsonia intracellularis
<220> FEATURE:
<221> NAME/KEY: misc_feature
<222> LOCATION: (1)...(846)
<223> OTHER INFORMATION: n = A,T,C or G

<400> SEQUENCE: 28
tatttactcg cgcggccggg cgtcttacac aaatggatcc cttgcantaa tccaaggata      60
acncctattg tganccatga acatcatcan natatcctct ttanatagca tcnannnntc     120
aannggaatt aacagttact anntagttaa tgtcatagta attgtcnata atatatgtaa     180
tcttaactaa ctaagctnnt taataataaa attnactact tatcaanaat aggtgatatn     240
gggttacatc ttgaaaatac ttnccataat tangagggct aatataatng aantaaaaag     300
accanatata aaaggaccag gccaaccaaa aaatgaccat ccaataccna aaacaattgg     360
cgaaaatact ctgacttaac ctcanaaatg tactgtttat agccatatca atagctctgt     420
tggatgtngg ngcaattgat gtaatgtggc tgtntactan angaaatgat ntacctcgtg     480
ctatncctan nacaanaata ngtaatgtaa gtanccnaat atcttggctt tgtaatggga     540
gaataatnnc aagtccttgg gaaatnaant tacnnccagc cagctatnnt aagcagttct     600
ntggtgacta tacgtcctac tnaantcgtg ccaaagatta aatanncgat aatcgcnctn     660
cctaaancan gcaatactaa aatggtttct nnctancttg gnatanggtg gaagcncgga     720
cagaattnan ttcgcnantt tanannggaa natncgtnaa nttantcggg gcccannccn     780
aaattcctna ntcnatanan naactnncctn ctntaaaang gccnactgga ntngttaaat     840
gaaata                                                                 846

<210> SEQ ID NO 29
<211> LENGTH: 855
<212> TYPE: DNA
<213> ORGANISM: Lawsonia intracellularis
<220> FEATURE:
<221> NAME/KEY: misc_feature
<222> LOCATION: (1)...(855)
<223> OTHER INFORMATION: n = A,T,C or G -continued

```
<400> SEQUENCE: 29
gattntttat cgatcactnt agacgcgatt tgggnaacac ttacctggta nccacccggg 60
tggaaaaatc gatgggcccg cggccgctct agaagtactc tcgagaagct ttttgaattc 120
tttggatcct caacacaggg tatggattaa aacaacttta gctctaacag gagcatttta 180
taatatattc cctggtagaa caatatctac tcaagaaaat ctgtctattg gttttcaact 240
aaaaaaaact tttaaacctt ttcattggac catcttactc ttagatgaac attatatgtc 300
ttcgccaaga attgcagcag caattatgcc tgcacagctt gctggagtta aaaacattat 360
agctgtttgg accagtaaaa ataaccgact gaccgctgaa aaaatctcac ctgctttact 420
aacaacatta gaactttcag gagttaacat agccctaaca cttacccaca ctgaaactga 480
acttcttatt catcaattaa tgaaaatagg tattggaaac ctgttatatt ttttaaaaga 540
agaagacata ctacatatat ctactatacc tgtactacct ttctggaaag aatatacttc 600
tcatcgactt gttatagaaa aagatgctgg cnttaataca gaaatcctcc aatgggcnca 660
tcctcattca attattgaac aaatagcaac agaaccatac tctgaaanat atcccagatg 720
cactttactg tgctagctca tccantaaaa actatnctca tanagnatcc ccagaatttt 780
tcatnatgga cttgaaccta tttggattca ncccaacnct tcctccaanc ctcctttctc 840
catacaccat gggga 855

<210> SEQ ID NO 30
<211> LENGTH: 1082
<212> TYPE: DNA
<213> ORGANISM: Lawsonia intracellularis
<220> FEATURE:
<221> NAME/KEY: misc_feature
<222> LOCATION: (1)...(1082)
<223> OTHER INFORMATION: n = A,T,C or G
<400> SEQUENCE: 30
tatctngttg antcaataaa acttttgggg cccntnaaan tttcatnann aaaaaaacaa 60
nattnctggg ggncccntcc caaaaaannc aatcantnng aancttgnct tcttattnng 120
nttttnanac tataatatnt nttatcnata atnnatcnnt atactnattt ctnattcant 180
nacanngggnn agnaanntta atctnaaana ctncnaaggg ggnnntnata ntntttnttt 240
ntttntcccn tnnaatnnat aaccnnncac ccnnattant tnnaatnnat accatancnn 300
cctttcaaac tgtacacata ntannnaann acactcnanc nttttncatc ctctctantn 360
ccnactccna tnnanctntt cccccatncc tatntntcnc tgcttcccag nttnnacntn 420
ncttnntttc acantattcc tatccaanct aacatntntn ntntcntnct ccttntntnt 480
tatntntttc tnntacctnn cactgacant ctatnantna nntcnnatac tnntatanct 540
ntangcnant ntatctanaa ntntancnnn nnatcntnac ngccgtnnat ntnnnnncan 600
ttanntannn ctancntnnc caannncnta tntatnaata acnactatcc natattnnat 660
tnnntnntnt cntanncaaa tnatttangc ncacnncact angtnatatn annattntat 720
attntgaanc ttctnggctt cncnaatant accantnnnc ancntcnnnt ncatctnnnt 780
ntacttcnta ccatancgct ctcnagnntc actacttcta ntagtnatcn tctactgccn 840
atggcnnnnn gcnnnncgan agntatncac ntacantnnc ntctactatn tanatctann 900
ncntccgnng cctncngtac gnntnggcna antcgnntac tttncntnta tctagtcnca 960
tcagnnntng antcctcaan cnngctctan ttacatgtnn nntnatgcnc tanancgnna 1020
```

```
cntctatcct tcnantctgc nctnantnta tanactctnn nnnatcnncn aanctatntc    1080
cc                                                                  1082
```

<210> SEQ ID NO 31
<211> LENGTH: 354
<212> TYPE: DNA
<213> ORGANISM: Lawsonia intracellularis
<220> FEATURE:
<221> NAME/KEY: misc_feature
<222> LOCATION: (1)...(354)
<223> OTHER INFORMATION: n = A,T,C or G

<400> SEQUENCE: 31

```
ctcccntnnc nctaagtgga ntcgcgcgct gcaggtcgac actagtggat cttgatatac      60
ttttaaaaga tgtgatgtta acatcaaaaa agcatgaatc acgttagact tgcagagtct     120
gtacatcaaa atattcttta cccaccttaa tacgaaaana aatnnttatn cnccncnatg     180
ggtggggntn aaatcctngc cccnttnccc tgttcnttta gggaaccccc naattccccn     240
ngttattcct ctgtttgaaa nttctggttn cccggccctn tnaccaanag cttgannncc     300 ncccgtcct ggggcatcct cntgtttatt ttccctcnan cnccccttn actn            354
```

<210> SEQ ID NO 32
<211> LENGTH: 477
<212> TYPE: DNA
<213> ORGANISM: Lawsonia intracellularis
<220> FEATURE:
<221> NAME/KEY: misc_feature
<222> LOCATION: (1)...(477)
<223> OTHER INFORMATION: n = A,T,C or G

<400> SEQUENCE: 32

```
ggatctttt gtgttttaca tggttttata ggaaatactt caagtttacc tggtcggggt       60
tcactatggt attgaagtac ttcttctttt gtnactaaag ccataaccgc tcctttaagt    120
tgttctcaaa aagaatatag tcttatatgt attaatctat ttactattgt atagatacaa    180
taggtcataa aaaatattct attattattc tactgttatt atatagaata taaatgtgtt    240
atggctattg taactcacaa tatgttgtat aaagcatgta tggttaaata cctaaattat    300
tgtnccagca tcaacaaaaa naattcaccg gttactcctg atganaggtc tgaagctaaa    360
aaaacagcag atttacctac atcttccata nttacattac gttttaatgg tgaatgttct    420
cctatataat taaaatttt tttgaagtcc aaatacnaaa gncgctaatg ttttata        477
```

<210> SEQ ID NO 33
<211> LENGTH: 568
<212> TYPE: DNA
<213> ORGANISM: Lawsonia intracellularis
<220> FEATURE:
<221> NAME/KEY: misc_feature
<222> LOCATION: (1)...(568)
<223> OTHER INFORMATION: n = A,T,C or G

<400> SEQUENCE: 33

```
gatcatttaa aaaaccatct tgagtaaaac gaaaattccc tgctcgtgta tagtgtactt      60
tatcctctaa tgtaacctga aaaaaacctt ttccaccaat agcaagatct gttacactat    120
tgccaggttc aaaagcaccc tgtgtaaaaa ttgtgcgaac acttccaacc tgtgctccca    180
taccagcctg gtttggcccc tgacttccag taaaacctat tgctaaatct tgactaaaca    240
ggtcttgaaa cactacctgt tgctgctat acccaatggt atttgcgtta gcaatattat    300
tggagacagt accanccctg tnctatgggt tttcatacct gttggcanca ataaacaaac    360
```

```
tccccatcat gataacatct cctaaaaaat aatttcatgg nggnaaaaat gttacctaca      420
catctctatt ttnaaagcaa aaaacccatg cccaanaaaa tttttgggcc naattaatat      480
acttaatcta ataaactttt ttgggtaatn aaaaaaaatt aatttttttaa acttggtttn     540 accaacctttt tctccttact ttttaacc                                        568

<210> SEQ ID NO 34
<211> LENGTH: 477
<212> TYPE: DNA
<213> ORGANISM: Lawsonia intracellularis
<220> FEATURE:
<221> NAME/KEY: misc_feature
<222> LOCATION: (1)...(477)
<223> OTHER INFORMATION: n = A,T,C or G

<400> SEQUENCE: 34
ggtaccccac ccgggtggaa aatcgatggg cccgcggccg ctctaaaant actctcgaga       60 agcttttttga attctttgga tccccaggaa taacttgttg acggaattttt acatttttcta  120 tccctgcaaa tanaaaaact ttaccttgta gttcattaat aggaaaagat tggagtactg     180
tgattccacc tgattgcgcc atagcttcta aaattagaac tccaggcatg acaggaaatc     240
caggggaaat gacccngaaa aaatggttca ttaatactaa cattttttata agctttaata   300 tatttgccag cattaaattc aataactcta tctacaatta aaaagggata acggtgggga    360
atttactgta aaatttcttg gatattttgg aggtatggat ggggacatta atttttcctat  420 atatatgctc tttttctttt cnaaaatttt tcagcttttt tatcccntaa aaacctc        477
```

THERAPEUTIC AND DIAGNOSTIC COMPOSITIONS

This is the U.S. national phase under 35 U.S.C. 371 of International Application PCT/AU96/00767.

FIELD OF INVENTION

The present invention relates generally to therapeutic compositions for the treatment and/or prophylaxis of intestinal disease conditions in animals and birds caused or exacerbated by *Lawsonia intracellularis* or similar or otherwise related microorganism. The present invention also contemplates methods for the treatment and/or prophylaxis of such intestinal disease conditions and to diagnostic agents and procedures for detecting *Lawsonia intracellularis* or similar or otherwise related microorganism.

BACKGROUND OF INVENTION

Bibliographic details of the publications numerically referred to in this specification are collected at the end of the description. Sequence Identity Numbers (SEQ ID NOs.) for the nucleotide and amino acid sequences referred to in the specification are defined following the bibliography.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

The meat industry in Australia and, indeed, in most countries of the world, is an important aspect of the overall livestock industry. However, the meat industry is subject to rapid economic downturn in response to disease conditions affecting the animals as well as human diseases putatively carried by the animals. It is important, therefore, to have well defined treatment, prophylactic and diagnostic procedures available to deal with infections or potential infections in animals and humans.

Pigs form a major component of the meat industry. However, pigs are sensitive to a wide spectrum of intestinal diseases collectively referred to as porcine proliferative enteropathy (PPE). This disease has previously been known as intestinal adentomatosis complex (1), porcine intestinal adenomatosis (PIA), necrotic enteritis (2), proliferative haemorrhagic enteropathy (3), regional ileitis (4), haemorrhagic bowel syndrome (5), porcine proliferative enteritis and *Campylobacter* spp induced enteritis (6).

There are two main forms of PPE: a non-haemorrhagic form represented by intestinal adenomatosis which frequently causes growth retardation and mild diarrhoea; and a haemorrhagic form, which is often fatal, represented by proliferative haemorrhagic enteropathy (PHE) where the distal small intestine lumen becomes engorged with blood. PPE has been reported in a number of animal species including pigs (14), hamsters (7), ferrets (15), guinea pigs (16), rabbits (17) as well as avian species (18).

The causative organism of PPE is a *Campylobacter*-like organism referred to herein as "*Lawsonia intracellularis*" (26). The organism has also been previously referred to as *Ileal symbiont intracellularis* (7). PPE-like diseases in pigs may also be caused by other pathogens such as various species of *Campylobacter* (8).

*Lawsonia intracellularis* is an intracellular, possibly obligate intracellular, bacterium. It can only be cultured in vitro with tissue culture cells (9, 26). Pigs suffering from PPE are characterised by multiple abnormal immature crypts and *L. intracellularis* is located in the cytoplasm of these crypt cells.

PPE is a significant cost component associated with the pig industry, especially in terms of stock losses, medication costs, reduced growth rates of pigs and increased feed costs. PPE also contributes to downstream indirect costs in, for example, additional labour costs and environmental costs in dealing with antibiotic residue contamination and in control measures to prevent the organism being passed on or carried to other animals or humans.

Current control strategies for PPE rely on the use of antibiotics. However, such a strategy is considered to be short to medium term especially as governmental regulatory pressures tend to target animal husbandry practices which are only supported by prophylactic antibiotics. There is a need, therefore, to develop effective, safe and low cost alternatives to the use of antibiotics. There is also a need to extend this alternative to antibiotics to similar organisms which infect other animals such as humans.

In work leading up to the present invention, the inventors sought to develop vaccines for the prophylaxis and treatment of PPE in animals and birds. The vaccines of the present invention provide an efficacious alternative to the use of antibiotics with a range of consequential husbandry and medical benefits.

SUMMARY OF THE INVENTION

Accordingly, one aspect of the present invention provides a vaccine composition for the prophylaxis or treatment of infection in an animal or bird by *L. intracellularis* or similar or otherwise related microorganism, said vaccine composition comprising an immunogenic, non-pathogenic form of *L. intracellularis* or related microorganism or an immunogenic component thereof and one or more carriers, diluents and/or adjuvants suitable for veterinary or pharmaceutical use.

The present invention is particularly useful and is exemplified hereinafter in relation to the protection and/or treatment of pigs from infection with *L. intracellularis*. However, this is done with the understanding that the present invention extends to the prophylaxis and treatment of all animals including humans and birds from infection with *L. intracellularis* and/or related microorganisms. Animals contemplated by the present invention include but are not limited to humans, primates, companion animals (e.g. cats, dogs), livestock animals (e.g. pigs, sheep, cattle, horses, donkeys, goats), laboratory test animals (e.g. mice, rats, guinea pigs, rabbits) and captive wild animals (e.g. kangaroos, foxes, deer). The present invention also extends to birds such as poultry birds, game birds and caged birds.

Furthermore, the present invention extends to all isolates and sub-types of *L. intracellularis* as well as other species of the genus *Lawsonia* or other microorganisms related thereto at the nucleotide, biochemical, structural, physiological and/or immunointeractive level. Reference hereinafter to "*Lawsonia intracellularis*" or its abbreviation "*L. intracellularis*" includes all microorganisms similar to or otherwise related to this microorganism. For example, a related microorganism may have a nucleotide sequence similarity at the chromosome or extrachromosomal level of at least about 60%, more preferably at least about 70% and even more preferably greater than at least about 80% with respect to all or part of a nucleotide sequence within the chromosome or extrachromosomal elements of *L. intracellularis*. For example, these percentage similarities may relate to the sequence set forth in SEQ ID NO:5. This sequence is a portion of the *L. intracellularis* chromosome.

Accordingly, this aspect of the present invention is directed to a vaccine composition for the prophylaxis and/or treatment of infection in a pig by *L. intracellularis*, said vaccine composition comprising an immunogenic, non-pathogenic form of *L. intracellularis* or related microorganism or an immunogenic component thereof and one or more carriers, diluents and/or adjuvants suitable for veterinary or pharmaceutical use.

The term "immunogenic component" refers to *L. intracellularis* (in attenuated non-pathogenic or killed form) or a component of *L. intracellularis* including a peptide, polypeptide or a protein encoded by DNA from or derived from *L. intracellularis* which is capable of inducing a protective immune response in a pig. A protective immune response may be at the humoural and/or cellular level and generally results in a substantial reduction in the symptoms of PPE in pigs. The vaccine compositions will comprise an effective amount of immunogenic component such as to permit induction of a protective immune response.

According to this aspect of the present invention there is provided a vaccine composition for the prophylaxis and treatment of a pig by *L. intracellularis*, said vaccine composition comprising an amount of at least one immunogenic component from *L. intracellularis* or related microorganism effective to induce a protective immune response in said pig against *L. intracellularis* or related microorganism, said vaccine composition further comprising one or more carriers, adjuvants and/or diluents suitable for veterinary or pharmaceutical use.

The immunogenic component may be a naturally occurring peptide, polypeptide or protein, a carbohydrate, lipid or nucleic acid (e.g. DNA) or any combination thereof isolated from *L. intracellularis* or a cell culture thereof or a recombinant form of a peptide, polypeptide or protein encoded by DNA from or derived from *L. intracellularis* or is a derivative of said peptide, polypeptide or protein.

An isolated component of *L. intracellularis* is a component which has undergone at least one purification step or which has undergone at least partial concentration from a cell culture comprising *L. intracellularis* or from a lysed preparation of *L. intracellularis* cells. The purity of such a component from *L. intracellularis* which has the requisite immunogenic properties is preferably at least about 40%, more preferably at least about 50%, even more preferably at least about 60%, still more preferably at least about 70% and even more preferably at least about 80–90% or greater relative to other components in a preparation as determined by molecular weight, immunogenic activity or other suitable means.

A particularly useful form of the vaccine is a whole cell vaccine which comprises *L. intracellularis* in attenuated or otherwise non-pathogenic form or killed cells or various fractions thereof.

Attenuated or non-pathogenic cells include killed *L. intracellularis* cells prepared, for example, by heat, formalin or other chemical treatment, electric shock or pressure and such cells are particularly useful in the practice of the present invention.

According to this aspect of the present invention there is provided a vaccine composition for the prophylaxis and/or treatment of infection in a pig by *L. intracellularis* or related microorganism said vaccine composition comprising a killed preparation of *L. intracellularis* or related microorganism or an immunogenic fraction thereof and one or more carriers, diluents and/or adjuvants suitable for veterinary or pharmaceutical use.

In an alternative embodiment, a recombinant vaccine may be employed. The recombinant vaccine may comprise one or more recombinant peptides, polypeptides or proteins derived from *L. intracellularis* or is a recombinant molecule immunologically related to a peptide, polypeptide or protein derived from *L. intracellularis* or may be a fusion molecule having a first portion comprising a peptide, polypeptide or protein derived from *L. intracellularis* and a second heterologous peptide, polypeptide or protein which may be useful, for example, as a carrier molecule or an adjuvant or an immune stimulating molecule such as cytokine. A particularly useful recombinant protein from *L. intracellularis* comprises a peptide, polypeptide or protein derived from the cell surface or membrane of *L. intracellularis*, is an enzyme in a metabolic pathway within *L. intracellularis* or is a refolding and/or heatshock protein. In a preferred embodiment, the protein is a refolding/heatshock protein such as but not limited to GroEL and GroES. Other putative vaccine candidates include flagellar basal body rod protein, S-adenosylmethionine: tRNA ribosyltransferase-isomerase, enoyl-(acyl-carrier-protein) reductase, N-acetyl muramoyl-L-alanine amidase (autolysin), UOP-3-0-[hydroxymyristoyl] glucosamine N-acetyltransferase and a glucarate transporter.

According to a preferred embodiment, the present invention relates to a vaccine composition for the prophylaxis and/or treatment of infection in a pig by *L. intracellularis* or related microorganism, said vaccine composition comprising at least one recombinant peptide, polypeptide or protein from *L. intracellularis* and wherein said recombinant peptide, polypeptide or protein is capable of inducing a protective immune response against *L. intracellularis* in pigs, the vaccine composition further comprising one or more carriers, diluents and/or adjuvants suitable for veterinary or pharmaceutical use.

In a particularly preferred embodiment, the recombinant protein is GroEL having an amino acid sequence as set forth in SEQ ID NO:2 or is a protein having a predicted amino acid sequence with at least about 40%, at least about 60%, or more preferably at least about 70% and even more preferably at least about 80–90% or greater similarity to all or part of the amino acid sequence set forth in SEQ ID NO:2.

In another embodiment, the recombinant molecule is GroES having an amino acid sequence as set forth in SEQ ID NO:4 or is a molecule having an amino acid sequence at least about 40%, at least about 60%, more preferably at least about 70% and even more preferably at least about 80–90% or greater similarity to all or part of the amino acid sequence set forth in SEQ ID NO:4.

Another embodiment of the present invention includes and comprises a peptide, polypeptide or protein encoded by a nucleotide sequence as set forth in SEQ ID NO:1 or having at least 40% similarity thereto or capable of hybridizing thereto under low stringency conditions and which nucleotide sequence encodes an immunogenic component of *L. intracellularis* or related microorganism.

In a related embodiment, the present invention includes and comprises a peptide, polypeptide or protein encoded by a nucleotide sequence as set forth in SEQ ID NO:3 or having at least 40% similarity thereto or capable of hybridizing thereto under low stringency conditions and which nucleotide sequence encodes an immunogenic component of *L. intracellularis* or related microorganism.

In a related embodiment, the present invention includes and comprises a peptide, polypeptide or protein encoded by a nucleotide sequence as set forth in SEQ ID NO:5 or having at least 40% similarity thereto or capable of hybridizing thereto under low stringency conditions and which nucleotide sequence encodes an immunogenic component of L. intracellularis or related microorganism.

In a related embodiment, the present invention includes and comprises a peptide, polypeptide or protein encoded by a nucleotide sequence as set forth in SEQ ID NO:6 or having at least 40% similarity thereto or capable of hybridizing thereto under low stringency conditions and which nucleotide sequence encodes an immunogenic component of L. intracellularis or related microorganism.

In a related embodiment, the present invention includes and comprises a peptide, polypeptide or protein encoded by a nucleotide sequence as set forth in SEQ ID NO:9 or having at least 40% similarity thereto or capable of hybridizing thereto under low stringency conditions and which nucleotide sequence encodes an immunogenic component of L. intracellularis or related microorganism.

In a related embodiment, the present invention includes and comprises a peptide, polypeptide or protein encoded by a nucleotide sequence as set forth in SEQ ID NO:12 or having at least 40% similarity thereto or capable of hybridizing thereto under low stringency conditions and which nucleotide sequence encodes an immunogenic component of L. intracellularis or related microorganism.

In a related embodiment, the present invention includes and comprises a peptide, polypeptide or protein encoded by a nucleotide sequence as set forth in SEQ ID NO:15 or having at least 40% similarity thereto or capable of hybridizing thereto under low stringency conditions and which nucleotide sequence encodes an immunogenic component of L. intracellularis or related microorganism.

In a related embodiment, the present invention includes and comprises a peptide, polypeptide or protein encoded by a nucleotide sequence as set forth in SEQ ID NO:21 or having at least 40% similarity thereto or capable of hybridizing thereto under low stringency conditions and which nucleotide sequence encodes an immunogenic component of L. intracellularis or related microorganism.

In a related embodiment, the present invention includes and comprises a peptide, polypeptide or protein encoded by a nucleotide sequence as set forth in SEQ ID NO:28 or having at least 40% similarity thereto or capable of hybridizing thereto under low stringency conditions and which nucleotide sequence encodes an immunogenic component of L. intracellularis or related microorganism.

In a related embodiment, the present invention includes and comprises a peptide, polypeptide or protein encoded by a nucleotide sequence as set forth in SEQ ID NO:29 or having at least 40% similarity thereto or capable of hybridizing thereto under low stringency conditions and which nucleotide sequence encodes an immunogenic component of L. intracellularis or related microorganism.

In a related embodiment, the present invention includes and comprises a peptide, polypeptide or protein encoded by a nucleotide sequence as set forth in SEQ ID NO:30 or having at least 40% similarity thereto or capable of hybridizing thereto under low stringency conditions and which nucleotide sequence encodes an immunogenic component of L. intracellularis or related microorganism.

In a related embodiment, the present invention includes and comprises a peptide, polypeptide or protein encoded by a nucleotide sequence as set forth in SEQ ID NO:31 or having at least 40% similarity thereto or capable of hybridizing thereto under low stringency conditions and which nucleotide sequence encodes an immunogenic component of L. intracellularis or related microorganism.

In a related embodiment, the present invention includes and comprises a peptide, polypeptide or protein encoded by a nucleotide sequence as set forth in SEQ ID NO:32 or having at least 40% similarity thereto or capable of hybridizing thereto under low stringency conditions and which nucleotide sequence encodes an immunogenic component of L. intracellularis or related microorganism.

In a related embodiment, the present invention includes and comprises a peptide, polypeptide or protein encoded by a nucleotide sequence as set forth in SEQ ID NO:33 or having at least 40% similarity thereto or capable of hybridizing thereto under low stringency conditions and which nucleotide sequence encodes an immunogenic component of L. intracellularis or related microorganism.

In a related embodiment, the present invention includes and comprises a peptide, polypeptide or protein encoded by a nucleotide sequence as set forth in SEQ ID NO:34 or having at least 40% similarity thereto or capable of hybridizing thereto under low stringency conditions and which nucleotide sequence encodes an immunogenic component of L. intracellularis or related microorganism.

Preferred percentage similarities include at least about 50% or at least about 60% or at least about 70–90%.

DETAILED DESCRIPTION OF THE PREFERRED EMBODIMENT

Figure 1:
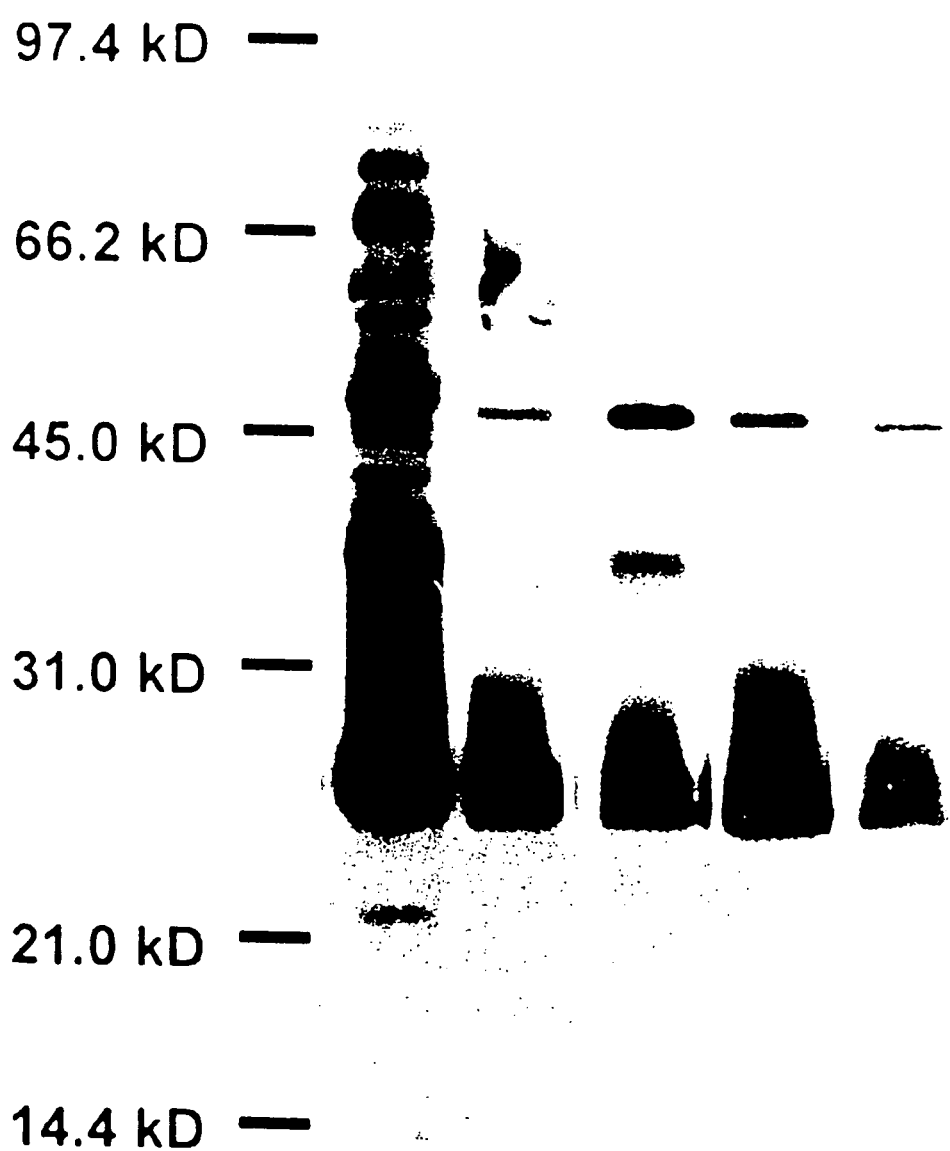
FIG. 1 is a photographic representation showing Western analysis of L. intracellularis antigens recognised by vaccinated pigs. Track 1 (395) was probed with pig sera from a pig (395) that had been immunised three times with the formalin killed whole L. intracellularis vaccine. Track 2 to 5 (Y10, Y12, Y14, Y16) were probed with sera obtained from pigs Y10, Y12, Y14 and Y16, respectively on day 0.

Reference herein to a low stringency at 42 EC includes and encompasses from at least about 1% v/v to at least about 15% v/v formamide and from at least about 1M to at least about 2M salt for hybridisation, and at least about 1M to at least about 2M salt for washing conditions. Alternative stringency conditions may be applied where necessary, such as medium stringency, which includes and encompasses from at least about 16% v/v to at least about 30% v/v formamide and from at least about 0.5M to at least about 0.9M salt for hybridisation, and at least about 0.5M to at least about 0.9M salt for washing conditions, or high stringency, which includes and encompasses from at least about 31% v/v to at least about 50% v/v formamide and from at least about 0.01M to at least about 0.15M salt for hybridisation, and at least about 0.01M to at least about 0.15M salt for washing conditions.

The present invention also contemplates peptides, polypeptides or proteins having an amino acid sequence substantially as set forth in one of SEQ ID NOs:7–8 or 10 or 11 or 13–14 or 16–20 or 22–27 or having at least 40% similarity thereof or to all or part thereof. Preferred percentage similarities include at least about 50%, or at least about 60% or at least about 70–90%.

The present invention further extends to a vaccine comprising a recombinant vaccine vector encoding a peptide, polypeptide or protein derived from *L. intracellularis* or related microorganism as described above. The vaccine vector may be of viral, yeast or bacterial origin and would be capable of expression of a genetic sequence encoding a peptide, polypeptide or protein from *L. intracellularis* in a manner effective to induce a protective immune response. For example, a non-pathogenic bacterium could be prepared containing a recombinant sequence capable of encoding a peptide, polypeptide or protein from *L. intracellularis*. The recombinant sequence would be in the form of an expression vector under the control of a constitutive or inducible promoter. The bacterium would then be permitted to colonise suitable locations in a pig's gut and would be permitted to grow and produce the recombinant peptide, polypeptide or protein in amount sufficient to induce a protective immune response against *L. intracellularis*.

In a further alternative embodiment, the vaccine may be a DNA vaccine comprising a DNA molecule encoding a peptide, polypeptide or protein from *L. intracellularis* and which is injected into muscular tissue or other suitable tissue in a pig under conditions sufficient to permit transient expression of said DNA to produce an amount of peptide, polypeptide or protein effective to induce a protective immune response.

The vaccines of the present invention may contain a single peptide, polypeptide or protein or a range of peptides, polypeptides or proteins covering different or similar epitopes. In addition, or alternatively, a single polypeptide may be provided with multiple epitopes. The latter type of vaccine is referred to as a polyvalent vaccine. A multiple epitope includes two or more repeating epitopes.

The formation of vaccines is generally known in the art and reference can conveniently be made to Remington's Pharmaceutical Sciences, 17th ed., Mack Publishing Co., Easton, Pa., USA.

The present invention, therefore, contemplates a pharmaceutical composition or vaccine composition comprising an immunity developing effective amount of one or more of:
(i) an immunogenic component from *L. intracellularis*;
(ii) a recombinant peptide, polypeptide or protein from *L. intracellularis* having immunogenic properties; and/or
(iii) whole cells or a component or fraction thereof from *L. intracellularis*.

The above components are referred to hereinafter as "active ingredients". The active ingredients of a vaccine composition as contemplated herein exhibit excellent therapeutic activity, for example, in the treatment and/or prophylaxis of PPE when administered in an amount which depends on the particular case. For example, for recombinant molecules, from about 0.5 µg to about 20 mg may be administered. Other useful effective amounts include 1 µg to about 10 mg, 10 µg to about 5 mg and 50 µg to about 1 mg. The important feature is to administer sufficient to induce an effective protective immune response. The above amounts may be administered as stated or may be calculated per kilogram of body weight. Dosage regime may be adjusted to provide the optimum therapeutic response. For example, several divided doses may be administered daily or the dose may be proportionally reduced as indicated by the exigencies of the therapeutic situation. Booster administration may also be required.

The active ingredients may be administered in a convenient manner such as by the oral, intravenous (where water soluble), intramuscular, subcutaneous, intranasal, intradermal or suppository routes or implanting (eg using slow release technology). Depending on the route of administration, the active ingredients which comprise, for example, peptides, polypeptides or proteins may be required to be coated in a material to protect said ingredients from the action of enzymes, acids and other natural conditions which may inactivate said ingredients.

The term "adjuvant" is used in its broadest sense and includes any immune stimulating compound such as interferon. Adjuvants contemplated herein include resorcinols, non-ionic surfactants such as polyoxyethylene oleyl ether and n-hexadecyl polyethylene ether and Freund's complete and incomplete adjuvant.

The active compounds may also be administered parenterally or intraperitoneally. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be fluid to the extent that easy syringability exists unless the pharmaceutical form is a solid or semi-solid such as when slow release technology is employed. In any event, it must be stable under the conditions of manufacture and storage and must be preserved against the contaminating action of microorganisms.

The carrier may be a solvent or dispersion medium containing, for example, water, ethanol, polyol (for example, glycerol, propylene glycol and liquid polyethylene glycol, and the like), suitable mixtures thereof and vegetable oils. The proper fluidity can be maintained, for example, by the use of a coating such as licithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

Carriers and diluents include any and all solvents, dispersion media, coatings, antibacterial and antifungal agents, isotonic and absorption delaying agents and the like. The use of such media and agents in vaccines is well known in the art. Except insofar as any conventional media or agent is incompatible with an active ingredient, use thereof in the therapeutic compositions is contemplated. Supplementary active ingredients can also be incorporated into the compositions.

Still another aspect of the present invention is directed to antibodies to the peptides, polypeptides or proteins from *L. intracellularis* or recombinant forms thereof or non-proteinaceous molecules such as carbohydrates. Such antibodies may be monoclonal or polyclonal and may be selected from naturally occurring antibodies to *L. intracellularis* or may be specifically raised to specific molecules or whole cells or components or fractions thereof. The antibodies of the present invention are particularly useful for immunotherapy and vaccination and may also be used as a diagnostic tool for infection or for monitoring the progress of a vaccination or therapeutic regime.

For example, recombinant *L. intracellularis* peptides, polypeptides or proteins can be used to screen for naturally occurring antibodies to *L. intracellularis*. Alternatively, specific antibodies can be used to screen for *L. intracellularis*. Techniques for such assays are well known in the art and include, for example, sandwich assays and ELISA. Hereinafter, an immunogenic component is considered to encompass an immunogenic component of *L intracellularis* and includes recombinant molecules, whole cells and cell extracts.

In accordance with this aspect of the present invention, the immunogenic components are particularly useful in screening for antibodies to *L. intracellularis* and, hence, provide a diagnostic protocol for detecting *L. intracellularis* infection. Alternatively, biological samples can be directly screened for *L. intracellularis* using antibodies raised to immunogenic components.

Accordingly, there is provided a method for the diagnosis of *L. intracellularis* infection in a pig comprising contacting a biological sample from said pig with an immunogenic component binding effective amount of an antibody for a time and under conditions sufficient for an immunogenic component-antibody complex to form, and then detecting said complex.

The presence of immunogenic components (or antibodies thereto) in a pig's blood, serum, or other bodily fluid, can be detected using a wide range of immunoassay techniques such as those described in U.S. Pat. Nos. 4,016,043, 4,424,279 and 4,018,653. This includes both single-site and two-site, or "sandwich", assays of the non-competitive types, as well as in the traditional competitive binding assays. Sandwich assays are among the most useful and commonly used assays and are favoured for use in the present invention. A number of variations of the sandwich assay technique exist, and all are intended to be encompassed by the present invention.

Briefly, in a typical forward assay, an immunogenic component-specific antibody is immobilised onto a solid substrate to form a first complex and the sample to be tested for immunogenic component brought into contact with the bound molecule. After a suitable period of incubation, for a period of time sufficient to allow formation of an antibody-immunogenic component secondary complex, a second immunogenic component antibody, labelled with a reporter molecule capable of producing a detectable signal, is then added and incubated, allowing sufficient time for the formation of a tertiary complex. Any unreacted material is washed away, and the presence of bound labelled antibody is determined by observation of a signal produced by the reporter molecule. The results may either be qualitative, by simple observation of the visible signal or may be quantitated by comparing with a control sample. The present invention contemplates a range of variations to the subject assay including an assay for *L. intracellularis* antibodies using, for example, recombinant peptides, polypeptides or proteins from this organism.

The solid substrate is typically glass or a polymer, the most commonly used polymers being cellulose, polyacrylamide, nylon, polystyrene, polyvinyl chloride or polypropylene. The solid supports may be in the form of tubes, beads, discs or microplates, or any other surface suitable for conducting an immunoassay. The binding processes are well-known in the art and generally consist of cross-linking covalently binding or physically adsorbing the molecule to the insoluble carrier.

By "reporter molecule", as used in the present specification, is meant a molecule which, by its chemical nature, produces an analytically identifiable signal which allows the detection of antigen-bound antibody. Detection may be either qualitative or quantitative. The most commonly used reporter molecule in this type of assay are either enzymes, fluorophores or radionuclide containing molecules (i.e. radioisotopes). In the case of an enzyme immunoassay, an enzyme is conjugated to the second antibody, generally by means of glutaraldehyde or periodate. As will be readily recognised, however, a wide variety of different conjugation techniques exist which are readily available to one skilled in the art. Commonly used enzymes include horseradish peroxidase, glucose oxidase, P-galactosidase and alkaline phosphatase, amongst others. The substrates to be used with the specific enzymes are generally chosen for the production, upon hydrolysis by the corresponding enzyme, of a detectable colour change. It is also possible to employ fluorogenic substrates, which yield a fluorescent product.

Alternatively, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state of excitability in the molecule, followed by emission of the light at a characteristic colour visually detectable with a light microscope. As in the EIA, the fluorescent labelled antibody is allowed to bind to the first antibody-hapten complex. After washing off the unbound reagent, the remaining ternary complex is then exposed to the light of the appropriate wavelength, the fluorescence observed indicates the presence of the hapten of interest. Immunofluorescence and EIA techniques are both very well established in the art and are particularly preferred for the present method. However, other reporter molecules, such as radioisotope, chemiluminescent or bioluminescent molecules, may also be employed. It will be readily apparent to the skilled technician how to vary the procedure to suit the required purpose.

A range of genetic diagnostic assays may be employed such as polymerase chain reaction (PCR) assays, hybridisation assays or protein truncation assays. All such assays are contemplated in the present invention.

| Amino Acid | Three-letter Abbreviation | One-letter Symbol |
| --- | --- | --- |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |

-continued

| Amino Acid | Three-letter Abbreviation | One-letter Symbol |
|---|---|---|
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any residue | Xaa | X |

SUMMARY OF THE SEQUENCE IDENTITY NUMBERS

| SEQ ID NO. | Description |
|---|---|
| 1 | Nucleotide sequence of GroEL |
| 2 | Amino acid sequence of GroEL |
| 3 | Nucleotide sequence of GroES |
| 4 | Amino acid sequence of GroES |
| 5 | Nucleotide sequence of L. intracellularis component |
| 6 | Nucleotide sequence of L. intracellularis component |
| 7 and 8 | Amino acid sequences of SEQ ID NO:6 |
| 9 | Nucleotide sequence of L. intracellularis component |
| 10 | Amino acid sequence of SEQ ID NO:9 (first coding sequence) |
| 11 | Amino acid sequence of SEQ ID NO:9 (second coding sequence) |
| 12 | Nucleotide sequence of L. intracellularis component |
| 13 and 14 | Amino acid sequences of SEQ ID NO:12 |
| 15 | Nucleotide sequence of L. intracellularis component |
| 16–20 | Amino acid sequences of SEQ ID NO:15 |
| 21 | Nucleotide sequence of L. intracellularis component |
| 22–27 | Amino acid sequences of SEQ ID NO:21 |
| 28 | Nucleotide sequence of L. intracellularis component |
| 29 | Nucleotide sequence of L. intracellularis component |
| 30 | Nucleotide sequence of L. intracellularis component |
| 31 | Nucleotide sequence of L. intracellularis component |
| 32 | Nucleotide sequence of L. intracellularis component |
| 33 | Nucleotide sequence of L. intracellularis component |
| 34 | Nucleotide sequence of L. intracellularis component |

The present invention is further described by reference to the following Examples.

EXAMPLE 1

Sources of Pig Tissue

Infected Pig Intestines

Sections of grossly thickened ilea were taken from pigs naturally or experimentally affected by PPE. The presence of *L. intracellularis* bacteria in the ilea was confirmed using immunofluorescent staining with specific monoclonal antibodies (10). An example of a suitable antibody is monoclonal antibody IG4 available from the University of Edinburgh, UK.

EXAMPLE 2

Isolation of *Lawsonia Intracellularis* Bacteria from the Infected Pig Ileum

*Lawsonia intracellularis* bacteria were extracted directly from lesions of PPE in pigs by filtration and further purified over a Percoll (Pharmacia, Uppsala, Sweden) gradient. Infected ilea were collected from pigs and the presence of *L. intracellularis* was confirmed histologically before storage at −80 EC. Sections of ileum were thawed and approximately 8 g of infected mucosa were scraped from the intestinal wall. The mucosa was homogenised with 40 ml sterile phosphate buffered saline (PBS) on half speed for 10 s using a Sorvall omnimixer. This suspension was centrifuged at 2000×g for 4 minutes. The supernatant was discarded and the cell pellet was resuspended in 40 ml PBS and recentrifuged. This washing step was repeated twice. The cell pellet was then resuspended in 20 ml PBS and homogenised at full speed for one minute to release *L. intracellularis* bacteria.

This homogenate was centrifuged at 1000×g for 4 minutes giving a pellet containing a crude mixture of homogenised epithelial cells and intestinal bacteria. The supernatant was filtered using filters with pore sized 3 Φm, 1.2 Φm and 0.8 Φm (Millipore Corporation, MA, USA). The filtrate was centrifuged at 8000×g for 30 minutes, resulting in a small pellet of *L. intracellularis* bacteria. The *L. intracellularis* bacteria were further purified using a 45% self forming percoll gradient as follows: 2 mls of the bacterial preparation was mixed by inversion into 30 mls of a 45% self forming Percoll (Pharmacia LKB, Uppsala, Sweden) gradient (45% v/v of Percoll, 150 mM NaCl). The gradients were centrifuged in a Sorval centrifuge using the SS34 rotor, at 20,000 rpm for 30 minutes at 4° C. Usually a number of bands form within the gradient. The band (usually located approx. 10–20 mm from the base of the tube) containing the *L. intracellularis* bacteria was collected and the volume made up to 16 mls with PBS. The solution was then centrifuged for 15 minutes at 800 rpm. The resultant pellet was washed with PBS before being resuspended in a final volume of approximately one ml.

EXAMPLE 3

Purification of *Lawsonia Intracellularis* Genomic DNA

Genomic DNA was extracted from percoll-gradient purified *Lawsonia intracellularis* bacteria, recovered from infected pig ilea scrapings (Example 2), by the methods described by Anderson et al (11) & Sambrook et al (12).

EXAMPLE 4

Immunoscreening Of Genomic Libraries

A lambda ZAP II *L. intracellularis* genomic library was plated on a lawn of *Escherichia coli* XLI-Blue (23) cells at a density of 2,000 plaque-forming units (pfu) per 150 mm L-broth agar plate. The library was screened with a rabbit anti-*L. intracellularis* sera using the method described in the Protoblot Technical Manual (Promega, Wis., USA). Filters were blocked in a buffer containing 10 mM Tris HCl, pH8.0, 150 mM NaCl, 0.05% Tween 20, 1% w/w gelatin. Positive plaques identified in a primary screen were picked, replated at a lower density and rescreened until individual positive plaques were identified.

EXAMPLE 5

Isolation and Sequencing of cDNA Inserts

Phagemid DNA from positive λZAP II phage clones was isolated by excision in vivo of the pBluescript phagemid under the conditions recommended by Stratagene (CA, USA). Plasmid DNA was either extracted by the method of Bimboim and Doly and the cDNA inserts sequenced by the chain termination method (21), or by the PEG-precipitation method and cycle-sequenced by the dye-terminator method, as recommended by the manufacturer (Applied Biosystems).

EXAMPLE 6

Antisera

Antisera to L. intracellularis bacteria were raised in rabbits and pigs. Rabbits were injected intramuscularly with a preparation of Percoll gradient-purified L. intracellularis bacteria mixed with a double-emulsion made by processing with oil adjuvant (Freund's incomplete adjuvant, CSL Limited, Melbourne, Australia), and then with Tween 80 enhancer. Two 3 ml injections, containing 9 mg protein, were given four weeks apart. Blood samples were collected from the marginal ear vein prior to immunisation and two weeks following the second injection.

A 6-week old pig (395) was hyperimmunised by intramuscular injection of Percoll gradient purified L. intracellularis bacteria prepared with Freund's incomplete adjuvant as for the rabbit. Three injections of the prepared antigen were administered four weeks apart, and blood was collected from the jugular vein two weeks following the final injection. Diluted pig sera (1 ml, 1 in 200) were pre-absorbed with 100 µl E. coli DH5α (24) lysate for 1 h at room temperature with gentle mixing. The lysate was prepared by freeze-thawing a suspension of E. coli in PBS.

EXAMPLE 7

Sodium Dodecyl Sulfate-Polyacrylamide Gel Electrophoresis (SDS-PAGE)

Protein samples were resuspended in 50 µl of sample buffer (62.4 mM HCl, 2% w/v SDS, 10% v/v glycerol, 5% v/v 20 mercaptoethanol, 0.002% bromophenol blue, pH 6.8) and heated to 95 EC for 5 minutes before separating solubilised proteins electrophoretically on a 0.1% w/v SDS-12% w/v PAGE vertical slab gel (13).

EXAMPLE 8

Western Blotting

Proteins were electrophoretically transferred to Immobilon-P (Millipore Corporation, MA, USA) membranes in a Trans-Blot Cell (BioRad, CA, USA) at 100 V for 1 h in a buffer containing CAPS (3-[Cyclohexylamino]-1-propanesulfonic acid, pH 11, Sigma, Mich., USA) and 10% v/v methanol. The membranes were then blocked with 5% w/v Blotto (Diploma skim milk powder, Melbourne, Australia) in PBS for 30 min at room temperature with gentle rocking. The filters were then transferred to antisera diluted in 5% w/v Blotto, PBS. Pre-absorbed pig antisera was diluted 1 in 200. The filters were incubated in pig antisera for 1 h followed by washing three times in PBST.

HRP conjugated anti-swine immunoglobulins (DAKO, Calif., USA) were applied at a dilution of 1:2000. Enhanced Chemiluminescence (ECL, Amersham, Ill., USA) was used to discriminate L. intracellularis proteins. Prior to ECL detection, blots were washed three times for 7 minutes each. The filters were exposed to autoradiographic film (Agfa, N.J., USA) for less than 1 minute before developing.

EXAMPLE 9

Identification of GroEL and GroES

Clones found to be positive according to the immunoscreening method described in Example 4 were sequenced using the protocol detailed in Example 5. One clone isolated represented the GroEL protein. The nucleotide sequence and corresponding amino acid sequence of GroEL are shown in SEQ ID NO: 1 and SEQ ID NO:2. Another clone isolated represented the GroES protein. The nucleotide sequence of GroES and corresponding amino acid sequence are shown in SEQ ID NO:3 and SEQ ID NO:4.

EXAMPLE 10

Immunoflorescent Detection of Lawsonia Intracellularis Bacteria in Pig Faeces

Faecal swabs of pigs were taken using a cotton tipped swab and then the sample was smeared onto a glass slide. After allowing ten minutes for air drying the smears were heat fixed by heating to 60° C. for approximately 10 seconds. The slides were then rinsed in PBS. An amount of 30 µl of a 1/200 dilution of a mouse ascites containing IG4 monoclonal antibody (see Example 1) was added, a glass cover slip applied, and the slides were incubated at room temperature for 40 minutes. The cover slip was removed and the slides were washed (PB ST for 7 minutes, three times). An amount of 30 µl of a 1/40 dilution of a FITC conjugated anti-mouse antiserum (Silenus, Melbourne Australia) was added, a glass cover slip applied and the slides were incubated at room temperature for 40 minutes. The cover slip was removed and the slides were washed (PBST for 7 minutes X3). The slides were given a final rinse in PBS. A drop of 10% v/v glycerol PBS was added and a glass cover slip applied. The fluorescent bacteria were visualised under highpower (×1200) at 340 nm using a Lietz laborlux S microscope. Twenty fields were counted and the results (see Table 1) were expressed as the average number of L. intracellularis bacteria per high powered field.

EXAMPLE 11

Formalin-Killed L. Intracellularis Vaccine

The percoll gradient purified bacterial L. intracellularis pellet was resuspended in 1 ml of 1 % formalin in saline and incubated overnight at 4° C. The percoll gradient-purified L. intracellularis bacteria was then mixed into a double-emulsion made by processing with oil adjuvant (Freund's incomplete adjuvant, Commonwealth Serum Laboratories, Melbourne, Australia), and then with Tween 80 enhancer.

EXAMPLE 12

Vaccination Protocol

Twelve weaned pigs (Landrace crossed with Large White) were sourced from a Pig Improvement Company piggery and treated with Neo-Terramycin (0.25 g/kilo) for 5 days. Seven days later (day −40) pigs Y10, Y12, Y14 and Y16 were vaccinated as described. Pigs Y3, Y11 and Y13 were treated for abscess with long acting terramycin on day −34.

The twelve pigs were divided into three groups and treated as follows:

Group 1 Infected Controls

Four pigs (Ear Tag No Y1–Y4) were housed with vaccinated pigs.

Group 2 Whole Bacteria Vaccine

Four pigs (Ear Tag No. Y10, Y12, Y14 and Y16) were immunised with 0.5 ml formalin killed *L. intracellularis* bacteria emulisifed in 0.5 ml of PBS/Freunds incomplete adjuvant on days −33 and −12.

Group 3 Uninfected Controls

Four pigs (Ear Tag No. Y9, Y11, Y13 and Y15) received no treatments and were housed in a separate area from the vaccinated pigs and infected control pigs.

EXAMPLE 13

Oral Challenges of Infected Pigs

Infected ilea were collected from pigs as described in Example 1 and the presence of *L. intracellularis* was confirmed histologically before storage at −80 EC. Sections of ileum were thawed and approximately 150 g of infected mucosa was scraped from the intestinal wall. The mucosa was homogenised with an equal volume of sterile PBS on half speed for 20 s using a Sorvall ominimixer. This suspension was diluted two fold with sterile PBS to form the challenge suspension.

On day 0 each pig from Groups 1 and 2 was dosed with a 5% w/v with Na Bicarbonate solution (10 ml/kg) followed by 30 ml of the challenge suspension. This was repeated on day 1 and day 2.

From day 11 onwards, the number of *L. intracellularis* bacteria in each pig's faeces was monitored by immunoflorescence. Pigs were monitored for signs of disease and shedding of *L intracellularis* bacteria. Pigs shedding greater than 100 bacteria per high powered field and scouring were killed for ethical reasons.

On day 22 the surviving pigs were humanely killed and the small intestines were recovered. Two sections of small intestine were removed 5 cms and 17 cms proximally from the ileocaecal junction. These sections were fixed in 10% v/v formalin, wax embedded and sections were sent to an independent veterinary pathologist for analysis.

EXAMPLE 14

*Lawsonia Intracellularis* Proteins Recognised by Vaccinated Pigs

Antibodies raised by pigs to *L. intracellularis* proteins post vaccination were analysed by Western blotting followed by ECL (Amersham, Ill., USA) detection as described in Example 8. The results are shown in FIG. 1. Vaccinated pigs produce antibodies to a range of *L. intracellularis* proteins. The most immunodominant proteins recognised are approximately 62.7 Kda, 58.7 Kda, 57.2 Kda, 44 Kda, 36.7 Kda and two smears from 24–26 Kda and 22–23.5 Kda. Minor immunoreactive bands had approximately the following molecular weights 67 Kda, 52.5 Kda, 50.5 Kda, 50 Kda, 48.2 Kda, 47.9 Kda, 44.7 Kda, 43.5 Kda, 42.5 Kda, 41.5 Kda, 40.5 Kda, 39 Kda, 35.3 Kda, 17 Kda, 15.5 Kda, 12 Kda and 7 Kda. The molecular weight of the proteins recognised will vary by up to 5% depending on the method used for estimation.

EXAMPLE 15

Shedding of *L. Intracellularis* Bacteria by Pigs During Trial

Three of the pigs from Group 1 (Infected control) in Example No. 12 (Y1, Y2 and Y4) shed greater than 100 *L. intracellularis* bacteria per high powered field in their faeces by day 19 post oral challenge (Table 1). Two of these pig (Y2 and Y4) had a bloody scour. All three pigs were humanely killed on day 20. Y3 shed low levels of *L. intracellularis* bacteria during the course of the infection trial. Maximal bacterial shedding for Y3 was 16 bacteria per high powered field.

All pigs in group 3 vaccinated with whole bacteria as set out in Example 12, never shed more than 3 *L. intracellularis* bacteria per high powered field. Vaccination with the formalin killed *L. intracellularis* vaccine reduced total bacterial shedding of *L. intracellularis* bacteria by vaccinated pigs by 98.5% when compared with group 1 pigs.

None of the group 3 pigs (uninfected controls) shed any *L. intracellularis* bacteria during the course of the trial.

The results of shedding of *L. intracellularis* bacteria per pig are shown in Table 1.

EXAMPLE 16

Gross Pathology for Trial A

Group 1 Infected Controls

Figure 2:
FIG. 2 is a photographic representation of the small intestine obtained from pig Y1 on day 20.

Y1 Approximately 5 cm of terminal ileum was grossly thickened. No other signs of PPE were evident macroscopically. Findings are consist with intestinal adenomatosis (See FIG. 2).

Figure 3:
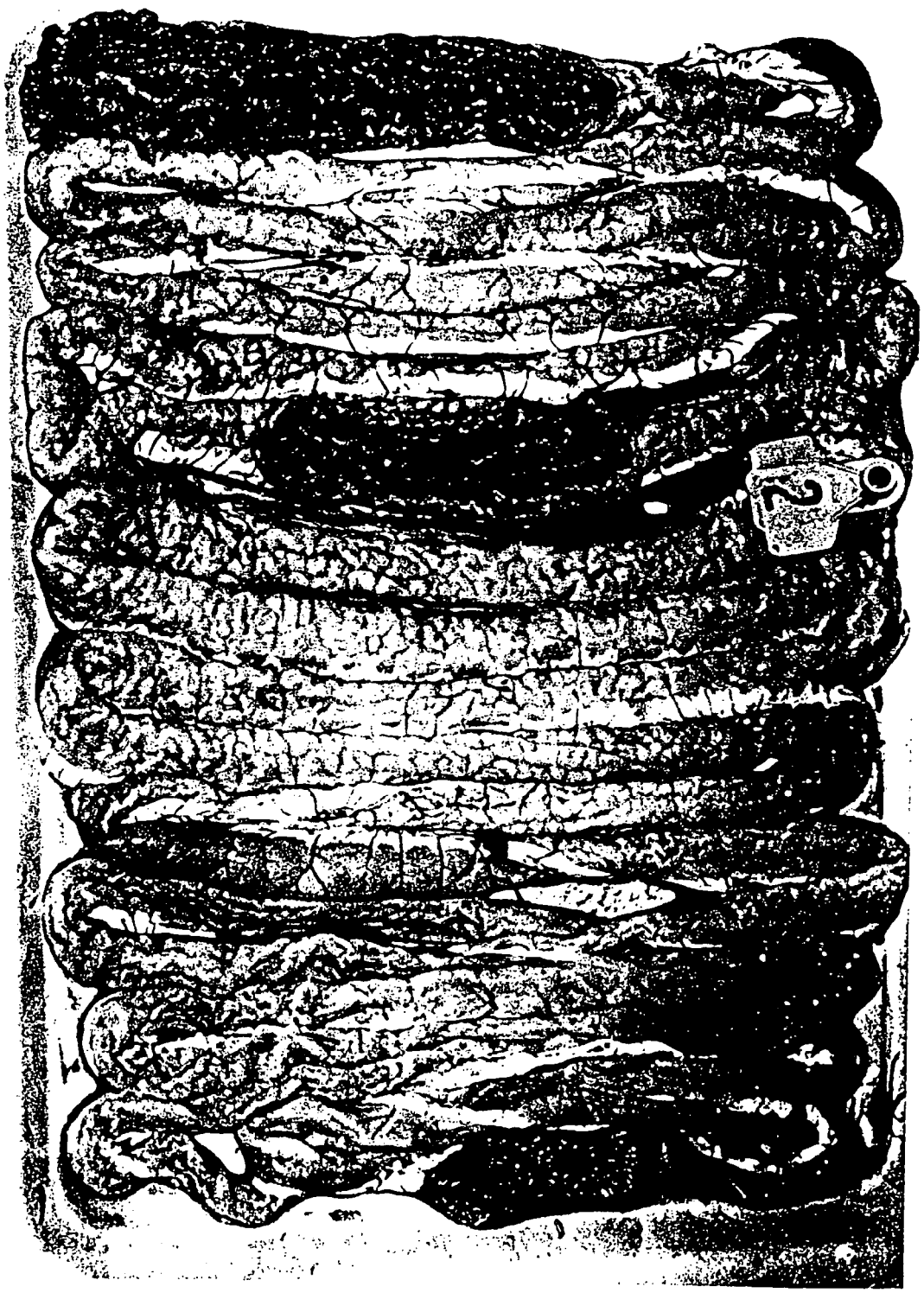
FIG. 3 is a photographic representation of the small intestine obtained from pig Y2 on day 20.

Y2 The intestine was found to be grossly thickened and the serosa had the characteristic cerebriform forms (FIG. 3). Over 2.5 meters of the intestine was involved. The lumen of the intestine was found to contain fresh blood and fibrinous casts were evident. Proliferative haemorrhagic enteropathy.

Y3 No gross signs of PPE were evident.

Figure 4:
FIG. 4 is a photographic representation of the small intestine obtained from pig Y4 on day 20.

Y4 The intestine was found to have necrotic enteritis (FIG. 4). The mucosal surface was replaced with a fibrinous pseudomembrane. Oedema of the mesentery was clearly evident. Over 2.0 meters of intestine was involved.

Group 2 Whole *L. Intracellularis* Cell Vaccine

Y10 No gross signs of PPE.
Y12 No gross signs of PPE.
Y14 No gross signs of PPE.
Y16 No gross signs of PPE.

Group 3 Uninfected Controls

Y9 No gross signs of PPE.
Y11 No gross signs of PPE.
Y13 No gross signs of PPE.
Y15 No gross signs of PPE.

EXAMPLE 17

Histopathology Report for Trial

Reports are based on established histopathological descriptions in Jubb et al (20).

Group 1 Infected Control Group

Y1 Numerous microfocal/confluent lesions of Porcine Intestinal Adenomatosis (PIA) are associated with Peyers Patches.

Y2 Serious generalised (annular) lesions of Porcine Intestinal Adenomatosis.

Y3 No conclusive evidence of PIA. Sparse microfocal lesions suggestive of a non-specific mild reactive (reparational) hyperplasia (rather than an adenomatosis).

Y4 Severe generalised (annular) lesions of PIA.

Group 2 Whole *L. Intracellularis* Cell Vaccine
Y10 No conclusive evidence of PIA.
Y12 No conclusive evidence of PIA.
Y14 No conclusive evidence of PIA.
Y16 No conclusive evidence of PIA. Possible single microfocus of PIA is associated with Peyers Patch.

Group 3 Uninfected Controls
Y11 No conclusive evidence of PIA.
Y9 No conclusive evidence of PIA.
Y13 Intestine was not recovered since pig was killed due to lameness at day 15.
Y 15 Diagnosis not possible because of the poor quality sections.

EXAMPLE 18

Immunoscreening of a *L. Intracellularis* Library Using Experimental Sera from Vaccinated Pigs

*L. intracellularis* genomic DNA was purified as described in Example 3. The DNA was partially digested with the restriction endonuclease Sau3 A (Promega) and ligated into Lambda ZAP II Express (Stratagene). The lambda library was plated on a lawn of *E. coli* XLI-Blue cells at a density of 10,000 pfu per 150 Mm L-broth agar plate. The library was screened, as described in Example 4, with sera from Y12. The pig Y12 was immunised with formalin killed *L. intracellularis*, as described in Example 11 & 12. Vaccinated pigs produced antibodies to a range of *L. intracellularis* proteins, as described in Example 14. A number of phage clones expressing *L. intracellularis* proteins were identified.

EXAMPLE 19

Analysis of *L. Intracellularis* Expressing Phage Clones

Phagemid DNA from positive λZAP II Express phage clones was isolated by in vivo excision, by the conditions recommended by the manufacturer (Stratagene). Plasmid DNA, for restriction analysis was extracted by alkaline-lysis, as described by Sambrook et al (12), and for automated sequencing, using the High Pure Plasmid Kit, as recommended by the manufacturer (Boehringer Mannheim). DNA sequencing of inserts was performed by the Dye-terminator method of automated sequencing (ABI Biosystems). The sequences identified are set out in SEQ ID NOS: 5 34 (see Example 20).

EXAMPLE 20

Identification of *L. Intracellularis* Components

Sequence similarity of the DNA molecules encoding putative vaccine candidates identified from Example 18 and 19, was identified using BLAST (27). Nucleotide sequence SEQ ID NO:6 and its corresponding amino acid sequences SEQ ID NOs:7 and 8 have sequence similarity to flagellar basal body rod protein. SEQ ID NO:9 (nucleotide) and SEQ ID NOS:10 and 11 (amino acid) have sequence similarity to autolysin. SEQ ID NO:12 (nucleotide) and SEQ ID NOs:13–14 (amino acid) show sequence similarity to S-adenosylmethionine: tRNA ribosyltransferase-isomerase (queuosine biosynthesis protein queA).

SEQ ID NO:15 (nucleotide) and SEQ ID NOs:16–20 (amino acid) show sequence similarity to enoyl-(acyl-carrier-protein) reductase. SEQ ID NO:21 (nucleotide) and SEQ ID NOs:22–27 (amino acid) show sequence similarity to a glucarate transporter. Other nucleotide sequences encoding putative vaccine candidates are SEQ ID NO:5, SEQ ID NO:28, SEQ ID NO:29, SEQ ID NO:30, SEQ ID NO:31, SEQ ID NO:32, SEQ ED NO:33 and SEQ ID NO:34.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

| Previous SEQ ID | Type of seq | Note | New SEQ ID | Type of seq |
|---|---|---|---|---|
| 1 | nt | 1 = 1 | 1 | nt |
| 2 | aa | 2 = 2 | 2 | aa |
| 3 | nt | 3 = 3 | 3 | nt |
| 4 | Aa | 4 = 4 | 4 | Aa |
| 5 | Nt (no CDS) | 5 = 5 | 5 | Nt (no CDS) |
| 6 | Nt | 6 = 6 | 6 | Nt |
| 7 | Aa | 7 = 7 + 8 | 7 | Aa |
|   |   |   | 8 | Aa |
| 8 | Nt | 8 = 9 | 9 | Nt |
| 9 | Aa | 9 = 10 | 10 | Aa |
| 10 | aa | 10 = 11 | 11 | Aa |
| 11 | Nt | 11 = 12 | 12 | Nt |
| 12 | Aa | 12 = 13 + 14 | 13 | Aa |
|   |   |   | 14 | Aa |
| 13 | Nt | 13 = 15 | 15 | Nt |
| 14 | Aa | 14 = 16 – 20 | 16 | Aa |
|   |   |   | 17 | Aa |
|   |   |   | 18 | Aa |
|   |   |   | 19 | Aa |
|   |   |   | 20 | Aa |
| 15 | Nt | 15 = 21 | 21 | Nt |
| 16 | Aa | 16 = 22 – 27 | 22 | Aa |
|   |   |   | 23 | Aa |
|   |   |   | 24 | Aa |
|   |   |   | 25 | Aa |
|   |   |   | 26 | Aa |
|   |   |   | 27 | Aa |
| 17 | Nt (no CDS) | 17 = 28 | 28 | Nt (no CDS) |
| 18 | Nt (no CDS) | 18 = 29 | 29 | Nt (no CDS) |
| 19 | Nt (no CDS) | 19 = 30 | 30 | Nt (no CDS) |
| 20 | Nt (no CDS) | 20 = 31 | 31 | Nt (no CDS) |
| 21 | Nt (no CDS) | 21 = 32 | 32 | Nt (no CDS) |
| 22 | Nt (no CDS) | 22 = 33 | 33 | Nt (no CDS) |
| 23 | Nt (no CDS) | 23 = 34 | 34 | Nt (no CDS) |

What is claimed is:

1. A composition for administration to an animal comprising an isolated immunogenic heatshock protein of *Lawsonia intracellularis* comprising the amino acid sequence of SEQ ID NO: 2 and a pharmaceutically acceptable carrier.

2. The composition according to claim 1, wherein the composition is formulated for administration to a pig.

3. The composition of claim 1, wherein the heatshock protein is produced by expression of a nucleic acid having the nucleotide sequence of SEQ ID NO:1.

4. The composition of claim 1, wherein said composition further comprises at least one other polypeptide or peptide comprising the amino acid sequence selected from the group consisting of: SEQ ID NO: 4, 7, 8, 10, 11, 13, 14, 16–20, and 22–27.

5. The composition of claim 1, further comprising at least one other protein or peptide, which is encoded by the nucleotide sequence selected from the group consisting of: SEQ ID NO: 3, 5, 6, 9, 12, 15, 21, 28, 29, 30, 31, 32, 33, and 34.

6. The composition of claim 1, further comprising at least one other protein or peptide from *L. intracellularis*, said protein or peptide selected from the group consisting of: a refolding protein, a flagellar basal body rod protein, an S-adenosylmethionine tRNA ribosyltransferase-isomerase, an autolysin, an enoyl-(acyl-carrier-protein) reductase, and a glucarate transporter.

7. A method of inducing an immune response in an animal against *L. intracellularis*, said method comprising the step of administering to said animal the composition of claim 1 in an amount effective to induce an immune response against *L. intracellularis* in said animal.

8. The method according to claim 7 wherein the animal is a pig.

9. The method according to claim 7, wherein said composition further comprises at least one immunogenic component from *L. intracellularis*, wherein said immunogenic component is a protein or peptide.

10. The method according to claim 9, wherein said protein or peptide is selected from the group consisting of a refolding protein, a flagellar basal body rod protein, an S-adenosylmethionine tRNA ribosyltrrsferase-isomerase, an autolysin, an enoyl-tacyl-carrier-protein) reductase, and a glucarate transporter.

* * * * *

UNITED STATES PATENT AND TRADEMARK OFFICE
CERTIFICATE OF CORRECTION

| | | |
|---|---|---|
| PATENT NO. | : 7,022,328 B1 | Page 1 of 1 |
| APPLICATION NO. | : 09/077574 | |
| DATED | : April 4, 2006 | |
| INVENTOR(S) | : Michael Panaccio and Detlef Hasse | |

It is certified that error appears in the above-identified patent and that said Letters Patent is hereby corrected as shown below:

On the Title Page, Item (73) Assignee, please add --Agriculture Victoria Services Pty. Ltd., Melbourne (Australia)--

In Claim 10, delete "ribosyltrrsferase" and insert therefore --ribosyltransferase--.

In Claim 10, delete "tacyl" and insert therefore --(acyl--.

Signed and Sealed this

Twenty-seventh Day of November, 2007

JON W. DUDAS
*Director of the United States Patent and Trademark Office*